United States Patent [19]
Chui et al.

[11] Patent Number: 5,939,599
[45] Date of Patent: Aug. 17, 1999

[54] HIGH SULFUR SEED PROTEIN GENE AND METHOD FOR INCREASING THE SULFUR AMINO ACID CONTACT OF PLANTS

[75] Inventors: Chok-Fun Chan Chui, Newark; Saverio Carl Falco, Arden; Janet Ann Rice, Wilmington, all of Del.; Susan Knowlton, Elkton, Md.

[73] Assignee: E. I. du Pont de Nemours and Company, Wilmington, Del.

[21] Appl. No.: 08/419,075

[22] Filed: Apr. 10, 1995

Related U.S. Application Data

[63] Continuation of application No. 08/098,371, filed as application No. PCT/US92/00958, Feb. 14, 1992, abandoned, which is a continuation of application No. 07/656,687, Feb. 14, 1991.

[51] Int. Cl.$^6$ .............................. A01H 5/00; C12N 15/82; C12N 15/09
[52] U.S. Cl. .................... 800/205; 800/230; 800/250; 800/DIG. 15; 800/DIG. 43; 800/DIG. 56; 800/DIG. 57; 536/23.1; 536/24.1; 530/370; 435/69.1; 435/172.3; 435/252.3
[58] Field of Search ..................... 800/205, 250, 800/230, DIG. 15, 43, 56, 57; 536/23.1, 24.1; 530/370; 435/69.1, 172.3, 252.3, 419

[56] References Cited

U.S. PATENT DOCUMENTS 5,258,300  11/1993  Glassman et al. .................... 435/240.4

FOREIGN PATENT DOCUMENTS

| 0 301 749 | 2/1989 | European Pat. Off. |
| WO 90/10076 | 9/1990 | WIPO ............................ C12N 15/82 |
| WO 91/02071 | 2/1991 | WIPO ............................ C12N 15/82 |

OTHER PUBLICATIONS

Philips et al, *Cereal Chem.*, 62, 213–218 (1985).
Madison et al, *Plant Cell Reports*, 7, 473–476 (1988).
Sambrook et al, *Molecular Cloning: A Laboratory Manual*, Cold Spring Harbor Laboratory Press (1989).
Chee et al *Plant Physiol.*, 91, 1212–1218 (1989).
Christou et al, *Proc. nat. Acad. Sci. USA*, 86, 7500–7504 (1989).
Hinchee et al, *Biotechnology*, 6, 915–922 (1989).
DeBlock et al, *Plant Physiol.*, 91, 694–701 (1989).
Gordon–Kamm et al, *Plant Cell*, 2, 603–618 (1990).
Fromm et al, *Biotechnology*, 8, 833–839 (1990).
Goldberg et al, *Cell*, 56, 149–160 (1989).
Thompson et al, *Bioessays*, 10, 108–113 (1989).
Pedersen et al, *J. Biol. Chem.*, 261, 6279–6284 (1984).
Kirihara et al, *Mol. Gen. Genet.*, 211, 477–484 (1988).
Kirihara et al, *Gene*, 71, 359–370 (1988).
Higgins et al, *J. Biol. Chem.*, 261, 11124–11130 (1986).
Altenbach et al, *Plant Mol. Biol*, 8, 239–250 (1987).
Masumura et al, *Plant Mol. Biol*, 12 123–130 (1989).
Beachy et al, *EMBO J.*, 4, 3047–3053 (1985).
Segupta–Gopalan et al., *Proc. Natl. Acad. USA*, 82, 3320–3324 (1985).
Barket et al, *Proc. Natl. Acad.Sci. USA*, 85, 458–462 (1988).
Ellis et al, *Plant. Mol. Biol.*, 10, 203–214 (1988).
Naito et al, *Plant. Mol. Biol*, 11, 109–123 (1988).
Hoffman et al, *Plant Mol. Biol.*, 11, 717–729 (1988).
Lawton et al, *Plant Mol. Biol.*, 9, 315–324 (1987).
Schernthaner et al, *EMBO J.*, 7, 1249–1255 (1988).
Ueng et al, *Plant Physiol.*, 86, 1281–1285 (1988).
Williamson et al, *Plant Physiol*, 88, 1002–1007 (1988).
Hoffman et al, *EMBO J.*, 6, 3213–3221 (1987).
Altenbach et al, *Plant Mol. Biol.*, 13, 513–522 (1988).
Altenbach et al, *Trends in Biotechnology*, 8(6), 156–160 (1990).
Norrander, et al, *Journal of Biotechnology*, 2, 157–175 (1985).
Masamura et al., *Plant Molecular Biology*, 12, 123–130 (1989).
Reeck, et al, *Cell*, 50, 667 (1987).
Dorel, et al, *J. Cell. Biology*, 108, 327–337 (1989).
Voelker, et al, *The Plant Cell*, 1, 95–104 (1989).
Nagy et al, *Biotechnology in Plant Science*, Academic Press, Inc., pp. 227–235 (1985).
von Heijne, *J. Mol. Biol.*, 173, 243–251 (1984).
Perlman et al, *J. Mol. Biol.*, 167, 391–409 (1983).
Iturriaga, et al, *The Plant Cell*, 1, 381–390 (1989).
Lewin, *Science*, 237, p. 1570 (1987).
Schickler et al, *The Plant Journal*, 3(2), 221–229 (1993).
Curtis, *Biology*, p. 70.
Krebbers et al, *Transgenic Plants: Fundamentals and Applications*, A Hiatt, Ed., 37–60 (1993).
Nielsen et al, *The Plant Cell*, 1, 313–328 (1989).
Vandekerckhove et al, *Bio/Technology*, 7, 929–932 (1989).
Rieger et al, *Glossary of Genetics*, Fifth Ed., Springer–Verlag, p. 453.
Walling, et al, *PNAS*, 83, 2123–2127 (1986).
Bustos et al, *EMBOS J*, 10, 1469–1479 (1991).
Baumlein et al, *The Plant Journal*, 2(2), 233–239 (1992).
Conceicao, et al, In Press: *Plant Molecular Biology*.
Goldberg, et al, *Cell*, 56, 149–160 (1989).
Altenbach et al (1989) Plant Mol. Biol 13:513–522.
Norrander et al (1985) J. Biotechnology 2:157–175.
Kunkel T.A.C. (1985) Proc. Natl Acad Sci USA 82:488–492.

*Primary Examiner*—Elizabeth F. McElwain

[57] ABSTRACT

There is provided a novel nucleic acid fragment for the overexpression of a high methionine seed storage protein in plants. This nucleic acid fragment is capable of transforming plants, particularly crop plants, to overexpress a corn seed storage protein in seeds or leaves. The invention is of significant interest for the nutritional improvement of sulfur amino acid-poor plants, such as corn and soybean. There is also provided chimeric genes, host cells, plants, seeds and microorganisms containing the nucleic acid fragment as well as methods for obtaining the overexpression of the seed storage protein in microorganisms.

19 Claims, 4 Drawing Sheets

FIG.1

```
10KD    1 MAAKMLALFALLALCASATSATHIPGHLPP.VMPLGTMNPCMQYCMMQQG  49
          |||||  |||||||||| ||||||||||| |   |||  ||||  |||||  |||
HSZ     1 MAAKMFALFALLALCATATSATHIPGHLSPLLMPLATMNPWMQYCMKQQG  50

10KD   50 LASLMACPSLMLQQLLALPLQ.............................  70
            |   |   |  |||||||||   |||
HSZ    51 VANLLAWPTLMLQQLLASPLQQCQMPMMMPGMMPPMTMMPMPSMMPSMMV 100

10KD   71 ........................TMPVMMPQMMTPNMMSPLMMPSMMS  95
                                     ||| |||  |   ||||  |||||
HSZ   101 PTMMSPMTMASMMPPMMMPSMISPMTMPSMMPSMIMPTMMSPMIMPSMMP 150

10KD   96 PMVLPSMMSQMMM......PQCHCDAVSQIMLQQQLPFMFNPMAMTIPPM 139
          ||  ||| | |||      |||    | |  |||||||| |  || ||||
HSZ   151 PMMMPSMVSPMMMPNMMTVPQCYSGSISHIIQQQQLPFMFSPTAMAIPPM 200

10KD  140 FLQQPFVGAAF 150
          |||||||||||
HSZ   201 FLQQPFVGAAF 211
```

HIGH SULFUR SEED PROTEIN GENE AND METHOD FOR INCREASING THE SULFUR AMINO ACID CONTACT OF PLANTS

This is a file-wrapper continuation application of Ser. No. 08/098,371, filed on Aug. 12, 1993, now abandoned which is a national stage application of PCT/US92/00958, filed Feb. 14, 1992, which is a continuation of Ser. No. 07/656,687 filed Feb. 14, 1991.

BACKGROUND OF THE INVENTION

The worldwide animal feed market, which includes livestock, poultry, aquaculture and pets is 475 million metric tons. In the United States 180 million metric tons are consumed with corn (God mays L.) accounting for about 67% and soybean (Glycine max L.) meal for about 10% of the total. Corn and soybean products are also a major element of foreign trade. These two crops are agronomically well-adapted to many parts of the U.S., and machinery and facilities for harvesting, storing and processing are widely available across the U.S. Because corn, soybean and other crops used for feed are currently sold as commodities, an excellent opportunity exists to upgrade the nutritional quality of the protein and thus add value for the U.S. farmer and enhance foreign trade.

Human food and animal feed derived from many grains are deficient in the sulfur amino acids, methionine and cysteine, which are required in the animal diet. In corn, the sulfur amino acids are the third most limiting amino acids, after lysine and tryptophan, for the dietary requirements of many animals. The use of soybean meal, which is rich in lysine and tryptophan, to supplement corn in animal feed is limited by the low sulfur amino acid content of the legume. Thus, an increase in the sulfur amino acid content of either corn or soybean would improve the nutritional quality of the mixtures and reduce the need for further supplementation through addition of more expensive methionine.

Efforts to improve the sulfur amino acid content of crops through plant breeding have met with limited success on the laboratory scale and no success on the commercial scale. A mutant corn line which had an elevated whole-kernel methionine concentration was isolated from corn cells grown in culture by selecting for growth in the presence of inhibitory concentrations of lysine plus threonine [Phillips et al. (1985) Cereal Chem. 62:213–218]. However, agronomically-acceptable cultivars have not yet been derived from this line and commercialized. Soybean cell lines with increased intracellular concentrations of methionine were isolated by selection for growth in the presence of ethionine [Madison and Thompson (1988) Plant Cell Reports 7:472–476], but plants were not regenerated from these lines.

The amino acid content of seeds is determined primarily by the storage proteins which are synthesized during seed development and which serve as a major nutrient reserve following germination. The quantity of protein in seeds varies from about 10% of the dry weight in cereals to 20–40% of the dry weight of legumes. In many seeds the storage proteins account for 50% or more of the total protein. Because of their abundance plant seed storage proteins were among the first proteins to be isolated. Only recently, however, have the amino acid sequences of some of these proteins been determined with the use of molecular genetic techniques. These techniques have also provided information about the genetic signals that control the seed-specific expression and the intracellular targeting of these proteins.

A number of sulfur-rich plant seed storage proteins have been identified and their corresponding genes have been isolated. A gene in corn for a 15 kD zein protein containing 11% methionine and 5% cysteine [Pedersen et al. (1986) J. Biol. Chem. 261:6279–6284] and a gene for a 10 kD zein protein containing 23% methionine and 3% cysteine have been isolated [Kirihara et al. (1988) Mol. Gen. Genet. 21:477–484; Kirihara et al. (1988) Gene 71:359–370]. Two genes from pea for seed albumins containing 8% and 16% cysteine have been isolated [Higgins et al. (1986) J. Biol. Chem. 261:11124–11130]. A gene from Brazil nut for a seed 2S albumin containing 18% methionine and 8% cysteine has been isolated [Altenbach et al. (1987) Plant Mol. Biol. 8:239–250]. Finally, from rice a gene coding for a 10 kD seed prolamin containing 19% methionine and 10% cysteine has been isolated [Masumura et al. (1989) Plant Mol. Biol. 12:123–130].

There have been many reports on the expression of seed storage protein genes in transgenic plants. The high-sulfur 2S albumin from Brazil nut has been expressed in the seeds of transformed tobacco under the control of the regulatory sequences from a bean phaseolin storage protein gene. The protein was efficiently processed from a 17 kD precursor to the 9 kD and 3 kD subunits of the mature native protein. The accumulation of the methionine-rich protein in the tobacco seeds resulted in an up to 30% increase in the level of methionine in the seeds [Altenbach et al. (1989) Plant Mol. Biol. 13:513–522]. Chimeric genes linking the coding regions of corn seed storage protein genes for 19 and 23 kD zeins to the Cauliflower Mosiac virus 35S promoter were expressed at very low levels in seeds, as well as roots and leaves, of transformed tobacco [Schernthaner et al. (1988) EMBO J. 7:1249–1255]. Replacement of the moncot regulatory regions (promoter and transcription terminator) with dicot seed-specific regulatory regions resulted in low level seed-specific expression of a 19 kD zein in transformed petunia [Williamson et al. (1988) Plant Physiol. 88:1002–1007] and tobacco [Ohtani et al. (1991) Plant Mol. Biol. 16:117–128]. In another case, high-level seed-specific expression of the 15 kD sulfur-rich zein was found in transformed tobacco, and the signal sequence of the monocot precursor was also correctly processed [Hoffman et al. (1987) EMBO J. 6:3213–3221].

In order to increase the sulfur amino acid content of seeds it is essential to isolate a gene(s) coding for seed storage proteins that are rich in the sulfur-containing amino acids methionine and cysteine. Methionine is preferable to cysteine because methionine can be converted to cysteine, but cysteine cannot be converted to methionine by most animals. It is desirable that the storage protein be compatible with those of the target crop plant. Furthermore, it is desirable that the protein come from a source that is generally regarded as safe for animal feed.

SUMMARY OF THE INVENTION

A means to increase the sulfur amino acid content of seeds has been discovered. Using the High Sulfur Zein (HSZ) gene chimeric genes may be created and used to transform various crop plants to increase the sulfur amino acid content of the seeds or leaves. Specifically, one aspect of the present invention is a nucleic acid fragment comprising a nucleotide sequence encoding the HSZ corn storage protein precursor corresponding to the sequence shown in SEQ ID NO:2:, or any nucleotide sequence substantially homologous therewith. Other aspects of the invention are those nucleic acid fragments encoding the mature HSZ protein (SEQ ID NO:3:) and encoding the High Methionine Domain (HMD) of the HSZ corn storage protein (SEQ ID NO:4:).

Other embodiments of this invention are chimeric genes capable of being expressed in transformed plants comprising any of the preceding nucleic acid fragments operably linked to regulatory sequences. Preferred are those chimeric genes which operably link the nucleic acid fragments to seed-specific promoters or promoters active in leaves of corn or soybean.

Another aspect of this invention is chimeric genes capable of being expressed in transformed microorganisms, preferably *E. coli*, to produce high sulfur proteins.

Yet another aspect of this invention are host cells transformed by chimeric genes to produce high sulfur proteins.

Yet other embodiments of the invention are transformed plants and the seeds derived from them containing any of the preceding nucleic acid fragments. Preferred are plants and the seeds derived from them selected from the group consisting of corn, soybeans, rapeseed, tobacco and rice.

Additional aspects of the invention are microorganisms transformed with the disclosed chimeric genes.

Further embodiments of the invention are methods for increasing the sulfur amino acid content of plants and *Agrobacterium tumefaciens* mediated methods for producing plants with the capacity to produce high sulfur proteins. Also encompassed within the invention are methods for producing protein rich in sulfur containing amino acids in a microorganism.

BRIEF DESCRIPTION OF THE DRAWINGS AND SEQUENCE DESCRIPTIONS

The invention can be more fully understood from the following detailed description, the accompanying drawings, and the Sequence Descriptions which form a part of this application. The Sequence Descriptions contain the three letter codes for amino acids as defined in 37 C.F.R. 1.822 which are incorporated by reference herein.

SEQ ID NO:1 shows the nucleotide sequence (2123 bp) of the corn HSZ gene and the predicted amino acid sequence of the primary translation product. Nucleotides 753–755 are the putative translation initiation codon and nucleotides 1386–1388 are the putative translation termination codon. Nucleotides 1–752 and 1389–2123 include putative 5' and 3' regulatory sequences, respectively.

SEQ ID NO:2 shows a preferred nucleotide sequence of the invention. It represents a 635 bp DNA fragment including the HSZ coding region only, which can be isolated by restriction endonuclease digestion using Nco I (5'-CCATGG) to Xba I (5'-TCTAGA). Two Nco I sites that were present in the native HSZ coding region were eliminated by site-directed mutagenesis, without changing the encoded amino acid sequence.

SEQ ID NO:3 shows a preferred nucleotide sequence of the invention. It represents a 579 bp DNA fragment including the coding region of the mature HSZ protein only, which can be isolated by restriction endonuclease digestion using BspH I (5'-TCATGA) to Xba I (5'-TCTAGA). Two Nco I sites that were present in the native HSZ coding region were eliminated by site-directed mutagenesis. This was accomplished without changing the encoded amino acid sequence.

SEQ ID NO:4 shows the nucleotide and derived amino acid sequence of the HMD gene.

SEQ ID NO:5 shows the DNA sequence of the corn 10 kD zein gene. [Kirihara et al. (1988) Mol. Gen. Genet. 21:477–484; Kirihara et al. (1988) Gene 71:359–370].

SEQ ID NOS:6 and 7 were used in Example 1 to screen a corn library for a high methionine 10 kD zein gene.

SEQ ID NOS:8 and 9 were used in Example 2 to carry out the mutagenesis of the HSZ gene.

SEQ ID NOS:10 and 11 were used in Example 2 to create a form of the HSZ gene with alternative unique endonuclease sites.

SEQ ID NOS:12 and 13 were used in Example 2 to create a gene to code for the mature form of HSZ.

SEQ ID NOS:14 and 15 were used in Example 5 to construct a gene to encode the HMD of HSZ.

SEQ ID NOS:16–21 were used in Example 6 the construction of chimeric genes for expression of HSZ in plants.

SEQ ID NO:22 was used in Example 7 for the analysis of transformants of tobacco with the Phaseolin-HSZ chimeric genes.

SEQ ID NOS:23, 24 and 25 were used in Example 10 for the construction of chimeric genes for expression of HMD in plants.

SEQ ID NQ:26 is a chimeric gene composed of the 35S promoter from Cauliflower Mosaic Virus [Odell et al.(1985) Nature 313:810–812], the hygromycin phosphotransferase gene from plasmid pJR225 (from *E. coli*) [Gritz et al.(1983) Gene 25:179–188] and the 3' region of the nopaline synthase gene from the T-DNA of the Ti plasmid of *Agrobacterium tumefaciens* used as a selectable genetic marker for transformation of soybean in Example 11.

SEQ ID NO:27 is the central region of the HSZ protein.

SEQ ID NO:28 is an amino acid sequence for the retention of proteins in the lumen of the endoplastic retriculum.

FIG. 1 shows a comparison of the amino acid sequences of the 10 kD zein (SEQ ID NO:5) and HSZ (SEQ ID NO:2). Single letter codes for amino acids are used. High methionine domains of the two proteins are underlined. The vertical lines in FIG. 1 indicate identical amino acid residues in the two proteins.

DETAILED DESCRIPTION OF THE INVENTION

Figure 2:
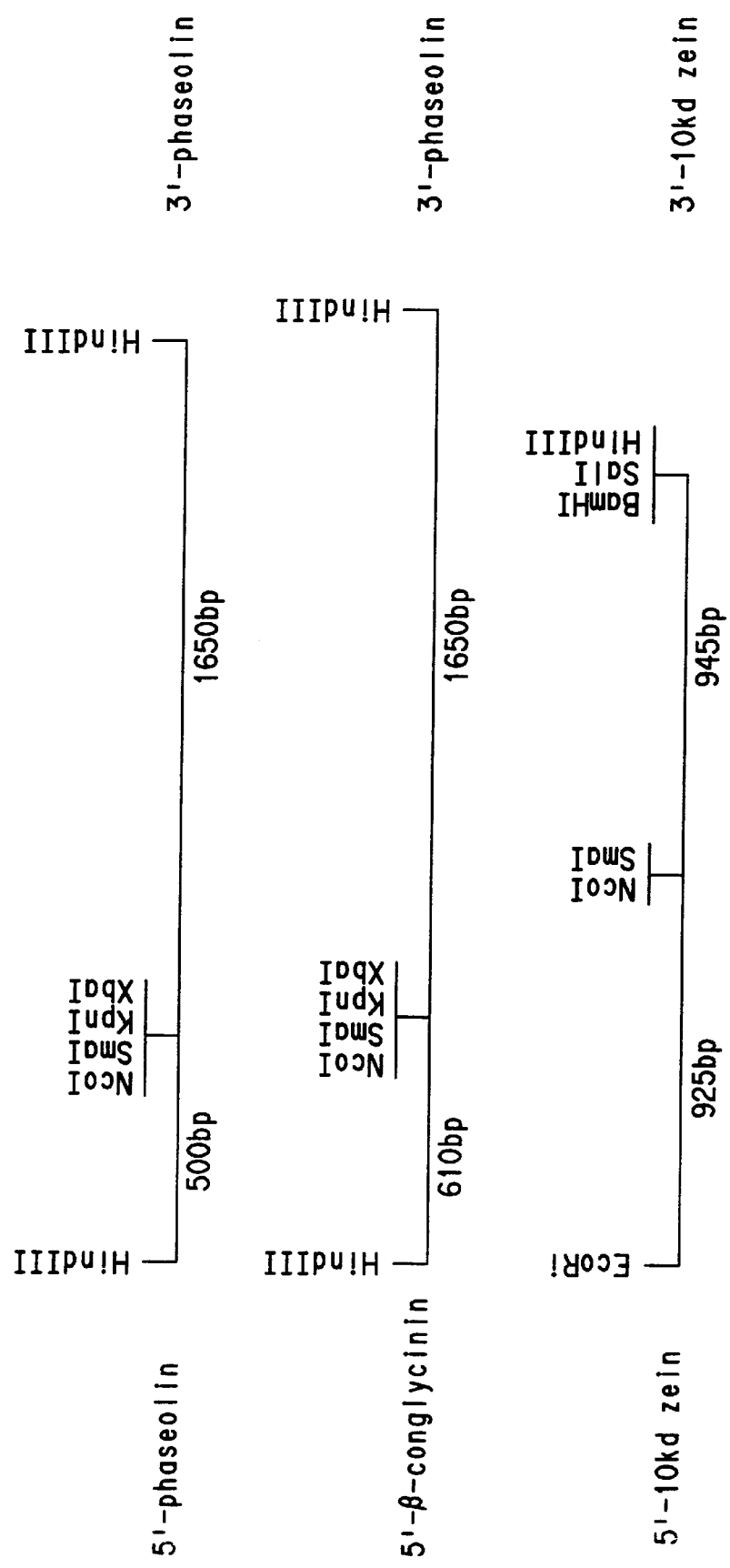
FIG. 2 shows a schematic representation of seed-specific gene expression cassettes useful for constructing chimeric genes for expression of HSZ in transgenic plants.

The present invention describes nucleic acid fragments that encode a corn High Sulfur Zein (HSZ) seed storage protein or a High Methionine Domain (HMD) derived from HSZ, both of which are unusually rich in the amino acid methionine.

The HSZ protein is composed of a central very-methionine-rich region (approximately 48% methionine residues) flanked by amino terminal and carboxy terminal regions with lower methionine content (10% methionine and 7% methionine, respectively). The central region is composed of variations of the repeating motif Met-Met-Met-Pro (SEQ ID NO:27). The related 10 kD zein protein has a similar but distinct structure (see FIG. 1). However the central region of the HSZ protein is about twice as large as the corresponding region in the 10 kD zein, accounting for the increased methionine content of HSZ. The apparent duplication of the central high methionine domain (HMD) in HSZ compared to 10 kD zein suggested that the central high methionine domain might have a stable structure and could be expressed by itself, yielding a very high methionine storage protein.

The introduction of a chimeric gene comprising seed storage protein regulatory sequences and methionine-rich seed storage protein coding sequence represents an approach to improve the nutritional quality of seeds from crop plants. The increase in methionine content of the seed will be determined by: (a) the level of expression of the chimeric gene in the transformed crop, which depends, in part, upon the seed-specific expression signals used, (b) the percentage of methionine residues in the seed storage protein coding region, (c) the stability of the introduced protein in the seed of the transformed crop plant, which depends, in part, upon its proper processing, intracellular targeting, assembly into higher-order structures in some cases, and ability to withstand dessication, and (d) the compatibility of the introduced protein with the native seed proteins of the transformed crop.

Transfer of the nucleic acid fragments of the invention, with suitable regulatory sequences, into a living cell will result in the production or overproduction of the protein. Transfer of the nucleic acid fragments of the invention into a plant, particulary corn, soybean or oilseed rape, with suitable regulatory sequences to direct expression of the protein in the seeds may result in an increased level of sulfur containing amino acids, particularly methionine, and thus improve the nutritional quality of the seed protein for animals.

In the context of this disclosure, a number of terms shall be utilized. As used herein, the term "nucleic acid" refers to a large molecule which can be single-stranded or double-stranded, composed of monomers (nucleotides) containing a sugar, phosphate and either a purine or pyrimidine. A "nucleic acid fragment" is a fraction of a given nucleic acid molecule. In higher plants, deoxyribonucleic acid (DNA) is the genetic material while ribonucleic acid (RNA) is involved in the transfer of the information in DNA into proteins. A "genome" is the entire body of genetic material contained in each cell of an organism. The term "nucleotide sequence" refers to a polymer of DNA or RNA which can be single- or double-stranded, optionally containing synthetic, non-natural or altered nucleotide bases capable of incorporation into DNA or RNA polymers.

As used herein, the term "homologous to" refers to the complementarity between the nucleotide sequence of two nucleic acid molecules or between the amino acid sequences of two protein molecules. Estimates of such homology are provided by either DNA-DNA or DNA-RNA hybridization under conditions of stringency as is well understood by those skilled in the art [as described in Hames and Higgins (eds.) Nucleic Acid Hybridisation, IRL Press, Oxford, U.K.]; or by the comparison of sequence similarity between two nucleic acids or proteins.

As used herein, "substantially homologous" refers to nucleic acid molecules which require less stringent conditions of hybridization than those for homologous sequences, and also refers to coding DNA sequence which may involve base changes that do not cause a change in the encoded amino acid, or which involve base changes which may alter one or more amino acids, but not affect the functional properties of the protein encoded by the DNA sequence. Thus, the nucleic acid fragments described herein include molecules which comprise possible variations of the nucleotide bases derived from deletion, rearrangement, random or controlled mutagenesis of the nucleic acid fragment, and even occasional nucleotide sequencing errors so long as the DNA sequences are substantially homologous.

"Gene" refers to a nucleic acid fragment that expresses a specific protein, including regulatory sequences preceding (5' non-coding) and following (3' non-coding) the coding region. "Native" gene refers to the gene as found in nature with its own regulatory sequences. "Chimeric" gene refers to a gene comprising heterogeneous regulatory and coding sequences. "Endogenous" gene refers to the native gene normally found in its natural location in the genome. A "foreign" gene refers to a gene not normally found in the host organism but that is introduced by gene transfer.

"Coding sequence" refers to a DNA sequence that codes for a specific protein and excludes the non-coding sequences. It may constitute an "uninterrupted coding sequence", i.e., lacking an intron, such as in a cDNA or it may include one or more introns bounded by appropriate splice junctions. An "intron" is a sequence of RNA which is transcribed in the primary transcript but which is removed through cleavage and re-ligation of the RNA within the cell to create the mature MRNA that can be translated into a protein.

"Initiation codon" and "termination codon" refer to a unit of three adjacent nucleotides in a coding sequence that specifies initiation and chain termination, respectively, of protein synthesis (mRNA translation). "Open reading frame" refers to the amino acid sequence encoded between translation initiation and termination codons of a coding sequence.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA" (MRNA) refers to the RNA that is without introns and that can be translated into protein by the cell. "cDNA" refers to a double-stranded DNA that is complementary to and derived from MRNA.

As used herein, "regulatory sequences" refer to nucleotide sequences located upstream (5'), within, and/or downstream (3') to a coding sequence, which control the transcription and/or expression of the coding sequences, potentially in conjunction with the protein biosynthetic apparatus of the cell. These nucleotide sequences include a promoter sequence, a translation leader sequence, a transcription termination sequence, and a polyadenylation sequence.

"Promoter" refers to a DNA sequence in a gene, usually upstream (5') to its coding sequence, which controls the expression of the coding sequence by providing the recognition for RNA polymerase and other factors required for proper transcription. A promoter may also contain DNA sequences that are involved in the binding of protein factors which control the effectiveness of transcription initiation in response to physiological or developmental conditions. It may also contain enhancer elements.

An "enhancer" is a DNA sequence which can stimulate promoter activity. It may be an innate element of the promoter or a heterologous element inserted to enhance the level and/or tissue-specificity of a promoter. "Constitutive promoters" refers to those that direct gene expression in all tissues and at all times. "Organ-specific" or "development-specific" promoters as referred to herein are those that direct gene expression almost exclusively in specific organs, such as leaves or seeds, or at specific development stages in an organ, such as in early or late embryo genesis, respectively.

The term "expression", as used herein, is intended to mean the production of the protein product encoded by a gene. "Overexpression" refers to the production of a gene product in transgenic organisms that exceeds levels of production in normal or non-transformed organisms.

The "3' non-coding sequences" refers to the DNA sequence portion of a gene that contains a transcription termination signal, polyadenylation signal, and any other regulatory signal capable of affecting mRNA processing or gene expression. The polyadenylation signal is usually characterized by affecting the addition of polyadenylic acid tracts to the 3' end of the mRNA precursor.

The "5' non-coding sequences" refers to the DNA sequence portion of a gene that contains a promoter sequence and a translation leader sequence.

The "translation leader sequence" refers to that DNA sequence portion of a gene between the promoter and coding sequence that is transcribed into RNA and is present in the fully processed mRNA upstream (5') of the translation start codon. The translation leader sequence may affect processing of the primary transcript to mRNA, mRNA stability or translation efficiency.

"Mature" protein refers to a post-translationally processed polypeptide without its signal peptide. "Precursor" protein refers to the primary product of translation of mRNA. "Signal peptide" refers to the amino terminal extension of a polypeptide, which is translated in conjunction with the polypeptide forming a precursor peptide and which is required for its entrance into the secretory pathway. The term "signal sequence" refers to a nucleotide sequence that encodes the signal peptide.

"Intracellular localization sequence" refers to a nucleotide sequence that encodes an intracellular targeting signal. An "intracellular targeting signal" is an amino acid sequence which is translated in conjunction with a protein and directs it to a particular sub-cellular compartment. "Endoplasmic reticulum (ER) stop transit signal" refers to a carboxy-terminal extension of a polypeptide, which is translated in conjunction with the polypeptide and causes a protein that enters the secretory pathway to be retained in the ER. "ER stop transit sequence" refers to a nucleotide sequence that encodes the ER targeting signal. Other intracellular targeting sequences encode targeting signals active in seeds and/or leaves and vascular targeting signals.

"Transformation" herein refers to the transfer of a foreign gene into the genome of a host organism and its genetically stable inheritance. Examples of methods of plant transformation include Agrobacterium-mediated transformation and accelerated-particle or "gene gun" transformation technology.

Recombinant DNA technology offers the potential for increasing the sulfur amino acid content of crop plants. Particularly useful technologies are: (a) methods for the molecular cloning and in vitro manipulation of genes [see Sambrook et al. (1989) Molecular Cloning: a Laboratory Manual, Cold Spring Harbor Laboratory Press], (b) introduction of genes via transformation into agriculturally-important crop plants such as soybean [Chee et al. (1989) Plant Physiol. 91:1212–1218; Christou et al. (1989) Proc. Nat. Acad. Sci U.S.A. 86:7500–7504; Hinchee et al. (1989) Biotechnology 6:915–922; EPO publication 0301 749 A2], rapeseed [De Block et al. (1989) Plant Physiol. 91:694–701], and corn [Gordon-Kamm et al. (1990) Plant Cell 2:603–618; Fromm et al. (1990) Biotechnology 8:833–839], and (c) seed-specific expression of introduced genes in transgenic plants [see Goldberg et al. (1989) Cell 56:149–160; Thompson and Larkins (1989) BioEssays 10:108–113]. In order to use these technologies to develop crop plants with increased sulfur amino acid content, it is essential to identify and isolate commercially-important genes.

Various solutions used in the experimental manipulations are referred to by their common names such as "SSC", "SSPE", "Denhardt's solution", etc. The composition of these solutions may be found by reference to Appendix B of Sambrook et al., (Molecular Cloning, a Laboratory Manual, 2nd ed. (1989), Cold Spring Harbor Laboratory Press).

CLONING OF THE CORN HSZ GENE

Based upon the published DNA sequence (SEQ ID NO:5) of the corn 10 kD zein gene [Kirihara et al. (1988) Mol. Gen. Genet. 21:477–484; Kirihara et al. (1988) Gene 71:359–370] oligonucleotides (SEQ ID NOS:6 and 7) were designed for use as primers for polymerase chain reaction (PCR) with genomic corn DNA as template. The product of the PCR reaction was isolated from an agarose gel and radioactively labelled by nick translation for use as a hybridization probe. A corn genomic DNA library in the vector λ-EMBL-3 was purchased from Clontech and plaques were screened with the PCR-generated probe. This was expected to result in the isolation of a full-length 10 kD zein gene including its 5' and 3' regulatory regions.

Two hybridizing λ plaques were purified and the cloned corn DNA fragment was further characterized. Restriction endonuclease digests and agarose gel electrophoresis indicated that the two clones were identical. The DNA fragments from the agarose gel were "Southern-blotted" onto nitrocellulose membrane filters and probed with radioactively-labeled 10 kD zein DNA generated by nick translation. A single 7.5 kb BamH I fragment and a single 1.4 kb Xba I fragment hybridized to the probe. These fragments were subcloned into phagemid pTZ18R (Pharmacia) for DNA sequence analysis.

Surprisingly, from the sequence it was evident that the gene isolated was related to, but distinct from, the 10 kD zein gene. It has been designated the High Sulfur Zein (HSZ) gene. The DNA fragment contains an open reading frame of 633 nucleotides, compared with the 453 nucleotides of the 10 kD zein gene. The HSZ protein shows 76% amino acid sequence identity with the 10 kD zein. However, the longer open reading frame of the HSZ gene codes for a methionine-rich domain not present in the 10 kD zein gene which results in a sulfur amino acid content of 29% (28% methionine) for the mature HSZ protein compared with 26% (22% methionine) for the 10 kD zein. Thus the HSZ gene codes for a seed storage protein which is the highest in methionine of any presently known. Well-known gene expression signals like the TATA box and polyadenylation signal were at similar positions in the HSZ and 10 kD zein genes. A putative 21 amino acid signal sequence is encoded by the HSZ gene at the amino terminus of the precursor polypeptide, similar to that of the 10 kD gene.

The DNA fragment of the instant invention may be used to isolate substantially homologous cDNAs and genes coding for seed storage proteins from corn and other plant species, particularly monocotyledenous plants. Isolation of related genes is well known in the art.

The use of restriction fragment length polymorphism (RFLP) markers in plant breeding has been well-documented in the art [see Tanksley et al. (1989) Bio. Technology 7:257–264]. The nucleic acid fragment of the invention can be mapped on a corn RFLP map. It can thus be used as a RFLP marker for traits linked to the mapped locus.

Modification of the HSZ Gene

The nucleic acid fragment of the instant invention coding for the sulfur-rich seed storage protein may be attached to suitable regulatory sequences and used to overproduce the protein in microbes such as *Escherichia coli* or yeast or in transgenic plants such as corn, soybean and other crop plants. Such a recombinant DNA construct may include either the native HSZ gene or a chimeric gene. One skilled in the art can isolate the coding sequences from the fragment of the invention by using and/or creating restriction endonuclease sites [see Sambrook et al. (1989) Molecular Cloning: A Laboratory Manual, Cold Spring Harbor Laboratory Press].

Of particular utility are naturally occuring sites for Nco I (5'-CCATGG) and Xba I (5'-TCTAGA) that allow precise removal of the coding sequence starting with the translation initiating codon ATG and ending with the translation stop codon TAG. However, three Nco I sites were present in the HSZ coding region. It was desirable to eliminate two of these sites and maintain only the one site (nucleotides 751–756 in SEQ ID NO:1) that included the translation start codon. A preferred DNA fragment of the invention (SEQ ID NO:2) was created by in vitro site-directed mutagenesis such that the two Nco I sites within the coding sequence have been removed without changing the amino acid sequence encoded by the gene. Thus a complete digest of the DNA with Nco I and Xba I yields a unique 637 bp fragment containing the entire coding sequence of the precursor HSZ polypeptide. To further facilitate the construction of chimeric genes, additional unique restriction endonuclease sites were added immediately following the translation stop signal of HSZ. Oligonucleotides (SEQ ID NOS.:10 and 11) were inserted into the Xba I site, introducing two new restriction sites, Sma I and Kpn I, and destroying the Xba I site. The now unique Xba I site from nucleotide 1–6 in SEQ ID NO:1 and the Ssp I site from nucleotide 1823–1828 in SEQ ID NO:1 were used to obtain a fragment that included the HSZ coding region plus its 5' and 3' regulatory regions. This fragment was cloned into the commercially available vector pTZ19R (Pharmacia) digested with Xba I and Sma I, yielding plasmid pCC10. Plasmid pCC10 was deposited on Dec. 7, 1990 at the ATCC, 12301 Parklawn Drive, Rockville, Md. 20852 under accession number 68490 under the terms of the Budapest Treaty.

In order to be able to express the mature form of the HSZ protein, it was desirable to create an altered form of the HSZ gene with a unique restriction endonuclease site at the start of the mature protein. To accomplish this a DNA fragment was generated using PCR. Oligonucleotide primers (SEQ ID NOS:12 and 13) were designed so that the PCR-generated fragment (SEQ ID NO:3) contained a BspH I site, which results in a cohesive-end identical to that generated by an Nco I digest. This site was located at the junction of the signal sequence and the mature HSZ coding sequence. The PCR-generated fragment also contained an Xba I site at the translation terminus of the HSZ gene.

A gene was constructed using PCR methodology to encode the high methionine domain (HMD) of HSZ. Oligonucleotides (SEQ ID NOS:14 and 15) were designed to add an Nde I site that included the translation initiation codon and an EcoR I site just past the translation termination codon (see SEQ ID NO:4). These sites permit easy insertion of HMD into expression vectors.

Expression of HSZ in *E. coli*

The HSZ coding sequence was expressed in *E. coli* using the bacteriophage T7 RNA polymerase/T7 promoter system [Studier et al. (1990) Methods in Enzymology 185:60–89]. The Nco I-Xba I fragment containing the HSZ coding sequence was inserted into an expression vector. This plasmid, designated pCC11, was expected to express the precursor HSZ protein. Additionally, a plasmid designed to express the HSZ protein without its signal sequence, designated pCC12, was constructed. The mature HSZ encoding DNA fragment for this construction was generated using PCR as described above and inserted into the expression vector.

To detect expression of the HSZ polypeptides plasmids PCC11 and pCC12 were transformed into *E. coli* strain HMS174 and an in vivo labelling experiment using $^{35}$S-methionine was performed as described by Studier and Moffatt [(1986) J. Mol. Biol. 189:113–130]. Because of the high methionine content of the HSZ protein this provides a specific and sensitive means for detection of expression. Cell extracts were run on SDS polyacrylamide gels which were dried and autoradiographed. A prominent labelled protein band of molecular weight about 20 kD was evident in both pCC11 and pCC12 extracts. This is the approximate size expected for the mature length HSZ polypeptide and suggested that the precursor protein made in the pCC11 transformant was being processed by *E. coli*. When total cell proteins were revealed by Coomassie brilliant blue staining following induction and SDS polyacrylamide gel electrophoresis, a prominent induced 20 kD protein was evident in the pCC12 lysates (but not in pCC11 lysates) indicating high level expression of the mature form of the protein.

The nucleic acid fragments of the invention can be used to produce large quantities of HSZ, HMD, or total protein enriched in sulfur-containing amino acids, particulary methionine, via fermentation of *E. coli* or other miroorganisms. To do this the nucleic acid fragment of the invention can be operably linked to a suitable regulatory sequence comprising a promoter sequence, a translation leader sequence and a 3' noncoding sequence. The chimeric gene can then be introduced into a microorganism via transformation and the transformed microorganism can be grown under conditions resulting in high expression of the chimeric gene. The cells containing protein enriched in sulfur-containing amino acids can be collected, and the enriched protein can be extracted. The HSZ protein can then be purified.

To produce large quantities of HSZ protein in *E. coli*, strain BL21 (DE3) pLysE [Studier et al. (1990) Methods in Enzymology 185:60–89] transformed with pCC12 was used. HSZ protein was purified from extracts of IPTG (isopropylthio-β-galactoside)-induced cultures. HSZ protein is found in an insoluble precipitate that can be easily collected by low-speed centrifugation of the cell extract. The majority of the cellular proteins are removed in the supernatant. HSZ is then selectively solubilized in a nearly (>90%) pure form from the centrifugation pellet by extraction with 70% isopropanol containing 10 mM β-mercaptoethanol. Between 10 and 100 mg of HSZ protein was obtained from one liter of cell culture. Because it has now been determined that production of the HSZ protein in *E. coli* is not toxic to the cells, higher levels of expression can be achieved using strain BL21 (DE3) [Studier et al. (1990) Methods in Enzymology 185:60–89].

Expression of HSZ in Plants

A preferred class of hosts for the expression of the coding sequence of HSZ or HMD are eukaryotic hosts, particularly the cells of higher plants. Particularly preferred among the higher plants and the seeds derived from them are soybean, rapeseed (*Brassica napus, B. campestris*), sunflower (*Helianthus annus*), cotton (*Gossypium hirsutum*), corn, tobacco (*Nicotiana Tubagum*), alfalfa (*Medicago sativa*), wheat (*Triticum* sp), barley (*Hordeum vulgare*), oats (*Avena sativa*, L), sorghum (*Sorahum bicolor*), rice (*Oryza sativa*), and forage grasses. Expression in plants will use regulatory sequences functional in such plants.

The expression of foreign genes in plants is well-established [De Blaere et al.(1987) Meth. Enzymol. 153:277–291]. The origin of promoter chosen to drive the expression of the coding sequence is not critical as long as it has sufficient transcriptional activity to accomplish the invention by increasing the level of translatable mRNA for HSZ or HMD in the desired host tissue. Preferred promoters for expression in all plant organs, and especially for expression in leaves include those directing the 19S and 35S transcripts in Cauliflower mosaic virus [Odell et al.(1985) Nature 313:810–812; Hull et al. (1987) Virology 86:482–493], small subunit of ribulose 1,5-bisphosphate carboxylase [Morelli et al.(1985) Nature 315:200; Broglie et al. (1984) Science 224:838; Hererra-Estrella et al.(1984) Nature 310:115; Coruzzi et al.(1984) EMBO J. 3:1671; Faciotti et al.(1985) Bio/Technology 3:241], maize zein protein [Matzke et al.(1984) EMBO J. 3:1525], and chlorophyll a/b binding protein [Lampa et al.(1986) ature 316:750–752].

Depending upon the application, it may be desirable to select promoters that are specific for expression in one or more organs of the plant. Examples include the light-inducible promoters of the small subunit of ribulose 1,5-bisphosphate carboxylase, if the expression is desired in photosynthetic organs, or promoters active specifically in seeds.

Preferred promoters are those that allow expression of the protein specifically in seeds. This may be especially useful, since seed& are the primary source of vegetable protein and also since seed-specific expression will avoid any potential deleterious effect in non-seed organs. Examples of seed-specific promoters include, but are not limited to, the promoters of seed storage proteins, which represent more than 50% of total seed protein in many plants. The seed storage proteins are strictly regulated, being expressed almost exclusively in seeds in a highly organ-specific and stage-specific manner [Higgins et al.(1984) Ann. Rev. Plant Physiol. 35:191–221; Goldberg et al.(1989) Cell 56:149–160; Thompson et al. (1989) BioEssays 10:108–113]. Moreover, different seed storage proteins may be expressed at different stages of seed development.

There are currently numerous examples for seed-specific expression of seed storage protein genes in transgenic dicotyledonous plants. These include genes from dicotyledonous plants for bean β-phaseolin [Sengupta-Gopalan et al. (1985) Proc. Natl. Acad. Sci. USA 82:3320–3324; Hoffman et al. (1988) Plant Mol. Biol. 11:717–729], bean lectin [Voelker et al. (1987) EMBO J. 6: 3571–3577], soybean lectin [Okamuro et al. (1986) Proc. Natl. Acad. Sci. USA 83:8240–8244], soybean kunitz trypsin inhibitor [Perez-Grau et al. (1989) Plant Cell 1:095–1109], soybean β-conglycinin [Beachy et al. (1985) EMBO J. 4:3047–3053; Barker et al. (1988) Proc. Natl. Acad. Sci. USA 85:458–462; Chen et al. (1988) EMBO J. 7:297–302; Chen et al. (1989) Dev. Genet. 10:112–122; Naito et al. (1988) Plant Mol. Biol. 11:109–123], pea vicilin [Higgins et al. (1988) Plant Mol. Biol. 11:683–695], pea convicilin [Newbigin et al. (1990) Planta 180:461], pea legumin [Shirsat et al. (1989) Mol. Gen. Genetics 215:326]; rapeseed napin [Radke et al. (1988) Theor. Appl. Genet. 75:685–694] as well as genes from monocotyledonous plants such as for maize 15 kD zein [Hoffman et al. (1987) EMBO J. 6:3213–3221; Schernthaner et al. (1988) EMBO J. 7:1249–1253; Williamson et al. (1988) Plant Physiol. 88:1002–1007], barley β-hordein [Marris et al. (1988) Plant Mol. Biol. 10:359–366] and wheat glutenin [Colot et al. (1987) EMBO J. 6:3559–3564]. Moreover, promoters of seed-specific genes operably linked to heterologous coding sequences in chimeric gene constructs also maintain their temporal and spatial expression pattern in transgenic plants. Such examples include *Arabidopsis thaliana* 2S seed storage protein gene promoter to express enkephalin peptides in Arabidopsis and *B. napus* seeds [Vandekerckhove et al. (1989) Bio/Technology 7:929–932], bean lectin and bean β-phaseolin promoters to express luciferase [Riggs et al. (1989) Plant Sci. 63:47–57], and wheat glutenin promoters to express chloramphenicol acetyl transferase [Colot et al. (1987) EMBO J. 6:3559–3564].

Of particular use in the expression of the nucleic acid fragment of the invention will be the heterologous promoters from several extensively-characterized soybean seed storage protein genes such as those for the Kunitz trypsin inhibitor [Jofuku et al. (1989) Plant Cell 1:1079–1093; Perez-Grau et al. (1989) Plant Cell 1:1095–1109], glycinin [Nielson et al. (1989) Plant Cell 1:313–328], β-conglycinin [Harada et al. (1989) Plant Cell 1:415–425]. Promoters of genes for α'- and β-subunits of soybean β-conglycinin storage protein will be particularly useful in expressing the HSZ mRNA in the cotyledons at mid- to late-stages of soybean seed development [Beachy et al. (1985) EMBO J. 4:3047–3053; Barker et al. (1988) Proc. Natl. Acad. Sci. USA 85:458–462; Chen et al. (1988) EMBO J. 7:297–302; Chen et al. (1989) Dev. Genet. 10:112–122; Naito et al. (1988) Plant Mol. Biol. 11:109–123] in transgenic plants, since: a) there is very little position effect on their expression in transgenic seeds, and b) the two promoters show different temporal regulation: the promoter for the α'-subunit gene is expressed a few days before that for the β-subunit gene.

Also of particular use in the expression of the nucleic acid fragments of the invention will be the heterologous promoters from several extensively characterized corn seed storage protein genes such as those from the 10 kD zein [Kirihara et al. (1988) Gene 71:359–370], the 27 kD zein [Prat et al. (1987) Gene 52:51–49; Gallardo et al. (1988) Plant Sci. 54:211–281], and the 19 kD zein [Marks et al. (1985) J. Biol. Chem. 260:16451–16459]. The relative transcriptional activities of these promoters in corn have been reported [Kodrzyck et al. (1989) Plant Cell 1:105–114] providing a basis for choosing a promoter for use in chimeric gene constructs for corn.

Proper level of expression of HSZ or HMD mRNA may require the use of different chimeric genes utilizing different promoters. Such chimeric genes can be transferred into host plants either together in a single expression vector or sequentially using more than one vector.

It is envisioned that the introduction of enhancers or enhancer-like elements into either the native HSZ promoter or into other promoter constructs will also provide increased levels of primary transcription for HSZ or HMD to accomplish the invention. This would include viral enhancers such as that found in the 35S promoter [Odell et al. (1988) Plant Mol. Biol. 10:263–272], enhancers from the opine genes [Fromm et al. (1989) Plant Cell 1:977–984], or enhancers from any other source that result in increased transcription when placed into a promoter operably linked to the nucleic acid fragment of the invention.

Of particular importance is the DNA sequence element isolated from the gene for the α'-subunit of β-conglycinin that can confer 40-fold seed-specific enhancement to a constitutive promoter [Chen et al. (1988) EMBO J. 7:297–302; Chen et al. (1989) Dev. Genet. 10:112–122]. One skilled in the art can readily isolate this element and insert it within the promoter region of any gene in order to obtain seed-specific enhanced expression with the promoter in transgenic plants. Insertion of such an element in any seed-specific gene that is expressed at different times than the β-conglycinin gene will result in expression in transgenic plants for a longer period during seed development.

The invention can also be accomplished by a variety of other methods to obtain the desired end. In one form, the invention is based on modifying plants to produce increased levels of HSZ protein by virtue of having significantly larger numbers of copies of the HSZ.

Any 3' non-coding region capable of providing a transcription termination signal, a polyadenylation signal and other regulatory sequences that may be required for the proper expression of the HSZ coding region can be used to accomplish the invention. This would include the native 3' end of the HSZ gene(s), the 3' end from a heterologous zein gene, the 3' end from any storage protein such as the 3' end of the soybean β-conglycinin gene, the 3' end from viral genes such as the 3' end of the 35S or the 19S cauliflower mosaic virus transcripts, the 3' end from the opine synthesis genes, the 3' ends of ribulose 1,5-bisphosphate carboxylase or chlorophyll a/b binding protein, or 3' end sequences from any source such that the sequence employed provides the necessary regulatory information within its nucleic acid sequence to result in the proper expression of the promoter/HSZ, or the promoter/HMD coding region combination to which it is operably linked. There are numerous examples in the art that teach the usefullness of different 3' non-coding regions [for example, see Ingelbrecht et al. (1989) Plant Cell 1:671–680].

DNA sequences coding for intracellular localization sequences may be added to the HSZ or HMD coding sequence if required for the proper expression of the proteins to accomplish the invention. Thus the native signal sequence of HSZ could be removed or replaced with a signal sequence known to function in the target plant. If the signal sequence were removed, the HSZ protein would be expected to remain in the cytoplasm of the cell. Alternatively, the monocot signal sequence of HSZ could be replaced by the signal sequence from the β subunit of phaseolin from the bean *Phaseolus vulparis*, or the signal sequence from the α' subunit of β-conglycinin from soybean [Doyle et al. (1986) J. Biol. Chem. 261:9228–9238], which function in dicot plants. Hoffman et al. [(1987) EMBO J. 6:3213–3221] showed that the signal sequence of the monocot precursor of a 15 kD zein directed the protein into the secretory pathway and was also correctly processed in transgenic tobacco seeds. However, the protein did not remain within the endoplasmic reticulum as is the case in corn. To retain the protein in the endoplasmic reticulum it may be necessary to add stop transit sequences. It is known in the art that the addition of DNA sequences coding for the amino acid sequence [lys-asp-glu-leu] (SEQ ID NO:28) at the carboxyl terminal of the protein retains proteins in the lumen of the endoplasmic reticulum [Munro et al. (1987) Cell 48:899–907; Pelham (1988) EMBO J. 7:913–918; Pelham et al. (1988) EMBO J. 7:1757–1762; Inohara et al. (1989) Proc. Natl. Acad. Sci. U.S.A. 86:3564–3568; Hesse et al. (1989) EMBO J. 8:2453–2461]. In some plants seed storage proteins are located in the vacuoles of the cell. In order to accomplish the invention it may be necessary to direct the HSZ or HMD protein to the vacuole of these plants by adding a vascular targeting sequence. A short amino acid domain that serves as a vascular targeting sequence has been identified from bean phytohemagglutinin which accumulates in protein storage vacuoles of cotyledons [Tague et al. (1990) Plant Cell 2:533–546]. In another report a carboxyl-terminal amino acid sequence necessary for directing barley lectin to vacuoles in transgenic tobacco was described [Bednarek et al. (1990) Plant Cell 2:1145–1155].

Construction of Chimeric Genes for Expression of HSZ in Plants

Three seed-specific gene expression cassettes were used for construction of chimeric genes for expression of HSZ in plants. The expression cassettes contained the regulatory regions from three highly expressed seed storage protein genes:

1) the β subunit of phaseolin from the bean *Phaseolus vulgaris*;

2) the α' subunit of β-conglycinin from soybean; and
3) the 10 kD zein from corn.

The cassettes are shown schematically in FIG. 2. They each have a unique Nco I site immediately following the 5' regulatory region and, in addition, some or all of the sites Xba I, Sma I and Kpn I immediately preceding the 3' regulatory region.

The Nco I-Xba I fragment containing the entire HSZ coding region (SEQ ID NO:2) and the BspH I-Xba I fragment containing the gene without the signal sequence, i.e. the mature protein coding sequence (SEQ ID NO:3), were inserted into the phaseolin and β-conglycinin expression cassettes (FIG. 2) which had been digested with Nco I and Xba I. For insertion into the 10 kD zein cassette, the Nco I-Sma I fragment containing the HSZ coding region was inserted into Nco I-Sma I digested 10 kD zein cassette.

Various methods of transforming cells of higher plants according to the present invention are available to those skilled in the art (see EPO publications 0 295 959 A2 and 0 138 341 A1). Such methods include those based on transformation vectors based on the Ti and Ri plasmids of Aarobacterium spp. It is particularly preferred to use the binary type of these vectors. Ti-derived vectors transformed a wide variety of higher plants, including monocotyledonous and dicotyledonous plants, such as soybean, cotton and rape [Pacciotti et al. (1985) Bio/Technology 3:241; Byrne et al. (1987) Plant Cell, Tissue and Organ Culture 8:3; Sukhapinda et al. (1987) Plant Mol. Biol. 8:209–216; Lorz et al. (1985) Mol. Gen. Genet. 199:178; Potrykus (1985) Mol. Gen. Genet. 199:183].

The phaseolin-HSZ chimeric gene cassettes were inserted into the vector pZS97K (FIG. 3) which is part of a binary Ti plasmid vector system [Bevan (1984) Nucl. Acids. Res. 12:8711–8720] of *Agrobacterium tumefaciens*. The vector contains: (1) the chimeric gene nopaline synthase/neomycin phosphotransferase (nos:NPT II) as a selectable marker for transformed plant cells [Bevan et al. (1983) Nature 304:184–186], (2) the left and right borders of the T-DNA of the Ti plasmid [Bevan (1984) Nucl. Acids. Res. 12:8711–8720], (3) the *E. coli* lacZ α-complementing segment [Vieria and Messing (1982) Gene 19:259–267] with unique restriction endonuclease sites for EcoR I, Kpn I, BamH I and Sal I, (4) the bacterial replication origin from the Pseudomonas plasmid pVS1 [Itoh et al. (1984) Plasmid 11:206–220], and 5) the bacterial neomycin phosphotransferase gene from Tn5 [Berg et al. (1975) Proc. Natl. Acad. Sci. U.S.A. 72:3628–3632] as a selectable marker for transformed *A. tumefaciens.*

The binary vectors containing the chimeric HSZ genes were transferred by tri-parental matings [Ruvkin et al. (1981) Nature 289:85–88] to Agrobacterium strain LBA4404/pAL4404 [Hockema et al (1983) Nature 303:179–180]. The Agrobacterium transformants were used to inoculate tobacco leaf disks [Horsch et al. (1985) Science 227:1229–1231]. Plants were regenerated in selective medium containing kanamycin.

Other transformation methods are available to those skilled in the art, such as direct uptake of foreign DNA constructs [see EPO publication 0 295 959 A2], techniques of electroporation [see Fromm et al. (1986) Nature (London) 319:791] or high-velocity ballistic bombardment with metal particles coated with the nucleic acid constructs [see Kline et al. (1987) Nature (London) 327:70, and see U.S. Pat. No. 4,945,050]. Once transformed the cells can be regenerated by those skilled in the art.

Of particular relevance are the recently described methods to transform foreign genes into commercially important crops, such as rapeseed [see De Block et al. (1989) Plant Physiol. 91:694–701], sunflower [Everett et al. (1987) Bio/Technology 5:1201], soybean [McCabe et al. (1988) Bio/Technology 6:923; Hinchee et al. (1988) Bio/Technology 6:915; Chee et al. (1989) Plant Physiol. 91:1212–1218; Christou et al. (1989) Proc. Natl. Acad. Sci USA 86:7500–7504; EPO Publication 0 301 749 A2], and corn [Gordon-Kamm et al. (1990) Plant Cell 2:603–618; Fromm et al. (1990) Biotechnology 8:833–839]

EXAMPLES

The present invention is further defined in the following EXAMPLES, in which all parts and percentages are by weight and degrees are Celsius, unless otherwise stated. It should be understood that these EXAMPLES, while indicating preferred embodiments of the invention, are given by way of illustration only. From the above discussion and these EXAMPLES, one skilled in the art can ascertain the essential characteristics of this invention, and without departing from the spirit and scope thereof, can make various changes and modifications of the invention to adapt it to various usages and conditions.

Example 1

Molecular Cloning of the HSZ Gene

A genomic library of corn in bacteriophage lambda was purchased from Clontech (Palo Alto, California). Data sheets from the supplier indicated that the corn DNA was from seven-day-old seedlings grown in the dark. The vector was λ-EMBL-3 carrying BamHI fragments 15 kb in average size. A titer of 1 to $9 \times 10^9$ plaque forming units (pfu)/mL was indicated by the supplier. Upon its arrival the library was titered and contained $2.5 \times 10^9$ pfu/mL.

The protocol for screening the library by DNA hybridization was provided by the vendor. About 30,000 pfu were plated per 150-mm plate on a total of 15 Luria Broth (LB) agar plates giving 450,000 plaques. Plating was done using E. coli LE392 grown in LB+0.2% maltose as the host and LB-7.2% agarose as the plating medium. The plaques were absorbed onto nitrocellulose filters (Millipore HATF, 0.45 mM pore size), denatured in 1.5M NaCl, 0.5M Tris-Cl pH 7.5, and rinsed in 3× SSC [Sambrook et al. (1989) Molecular Cloning: A Laboratory Manual, Cold Spring Harbor Laboratory Press]. The filters were blotted on Whatman 3MM paper and heated in a vacuum oven at 80° C. for two hours to allow firm anchorage of phage DNA in the membranes.

A hybridization probe was generated to screen the library for a high methionine 10 kD zein gene [Kirihara et al. (1988) Mol. Gen. Genet. 211:477–484] along with its 5' and 3' flanking regions. Two oligonucleotides 30 bases long flanking this gene were synthesized using an Applied Biosystems DNA synthesizer. Oligomer SM56 (SEQ ID NO:6) codes for the positive strand spanning the first ten amino acids:

```
SM56  5'-ATG GCA GCC AAG ATG CTT GCA TTG TTC GCT-3'    (SEQ ID NO:6)
         Met Ala Ala Lys Met Leu Ala Leu Phe Ala       (amino acids
                                                        -21 to -12 of
                                                        SEQ ID NO:5)
```

Oligomer CFC77 (SEQ ID NO:7) codes for the negative strand spanning the last ten amino acids:

```
CFC77 3'-AAT GTC GTT GGG AAA CAA CCA CGA CGT AAG-5'    (SEQ ID NO:7)
         Leu Gln Gln Pro Phe Val Gly Ala Ala Phe       (amino acids
                                                        120 to 129 of
                                                        SEQ ID NO:5)
```

These were employed to generate by polymerase chain reaction (PCR) the 10 kD coding region using maize genomic DNA (B85 strain) as the template. PCR was performed using a Perkin-Elmer Cetus kit according to the instructions of the vendor on a thermocycler manufactured by the same company. The reaction product when run on a 1% agarose gel and stained with ethidium bromide showed a strong DNA band of the size expected for the 10 kD zein gene, 450 bp, with a faint band at about 650 bp. The 450 bp band was electro-eluted onto DEAE cellulose membrane (Schleicher & Schuell) and subsequently eluted from the membrane at 65° C. with 1M NaCl, 0.1 mM EDTA, 20 mM Tris-Cl, pH 8.0. The DNA was ethanol precipitated and rinsed with 70% ethanol and dried. The dried pellet was resuspended in 10 μL water and an aliquot (usually 1 μL) was used for another set of PCR reactions, to generate by asymmetric priming single-stranded linear DNAs. For this, the primers SM56 and CFC77 were present in a 1:20 molar ratio and 20:1 molar ratio. The products, both positive and negative strands of the 10 kD zein gene, were phenol extracted, ethanol precipitated, and passed through NACS (Bethesda Research Laboratories) columns to remove the excess oligomers. The eluates were ethanol precipitated twice, rinsed with 70% ethanol, and dried. DNA sequencing was done using the appropriate complementary primers and a sequenase kit from United States Biochemicals Company according to the vendors instructions. The sequence of the PCR product was identical to the published sequence of the 10 kD zein gene. A radioactive probe was made by nick-translation of the PCR-generated 10 kD zein gene using $^{32}$P-dCTP and a nick-translation kit purchased from Bethesda Research Laboratories.

The fifteen 150-mm nitrocellulose filters carrying the λ phage plaques were screened using radioactive 10 kD gene probe. After four hours prehybridizing at 60° C. in 50× SSPE, 5× Denhardt's, [see Sambrook et al. (1989) Molecular Cloning: A Laboratory Manual, Cold Spring Harbor Laboratory Press] 0.1% SDS, 100 g/mL calf thymus DNA, the filters were transferred to fresh hybridization mix containing the denatured radiolabeled 10 kD zein gene (cpm/mL) and stored overnight at 60° C. They were rinsed the following day under stringent conditions: one hour at room temp in 2× SSC—0.05% SDS and one hour at 68° C. in 1× SSC—0.1% SDS. Blotting on 3MM Whatman paper followed, then air drying and autoradiography at –70° C. with Kodak XAR-5 films with Du Pont Cronex® Lightning Plus intensifying screens. From these autoradiograms, 20 hybridizing plaques were identified. These plaques were picked from the original petri plate and plated out at a dilution to yield about 100 plaques per 80-mm plate. These plaques were absorbed to nitrocellulose filters and re-probed using the same procedure. After autoradiography only one of the original plaques, number 10, showed two hybridizing plaques. These plaques were tested with the probe a third time; all the progeny plaques hybridized, indicating that pure clones had been isolated.

DNA was prepared from these two phage clones, λ10-1, λ10-2, using the protocol for DNA isolation from small-scale liquid λ-phage lysates (Ansul et al. (1987) Current Protocols in Molecular Biology, pp. 1.12.2, 1.13.5–6). Restriction endonuclease digests and agarose gel electrophoresis showed the two clones to be identical. The DNA fragments from the agarose gel were "Southern-blotted" [see Sambrook et al. (1989) Molecular Cloning: A Laboratory Manual, Cold Spring Harbor Laboratory Press] onto nitrocellulose membrane filters and probed with radioactively-labeled 10 kD zein DNA generated by nick translation. A single 7.5 kb BamH I fragment and a single 1.4 kb Xba I fragment hybridized to the probe.

The 7.5 kb BamH I fragment was isolated from a BamH I digest of the λDNA run on an 0.5% low melting point (LMP) agarose gel. The 7.5 kb band was excised, melted, and diluted into 0.5M NaCl and loaded onto a NACS column, which was then washed with 0.5M NaCl, 10 mM Tris-Cl, pH 7.2, 1 mM EDTA and the fragment eluted with 2M NaCl, 10 mM Tris-Cl, pH 7.2, 1 mM EDTA. This fragment was ligated to the phagemid pTZ18R (Pharmacia) which had been cleaved with BamH I and treated with calf intestinal alkaline phosphatase [see Sambrook et al. (1989) Molecular Cloning: A Laboratory Manual, Cold Spring Harbor Laboratory Press] to prevent ligation of the phagemid to itself. Subclones with these fragments in both orientations with respect to the pTZ18R DNA were obtained following transformation of E. coli.

An Xba I digest of the cloned λphage DNA was run on an 0.8% agarose gel and a 1.4 kb fragment was isolated using DEAE cellulose membrane (same procedure as for the PCR-generated 10 kD zein DNA fragment described above). This fragment was ligated to pTZ18R cut with Xba I in the same way as described above. Subclones with these fragments in both orientations with respect to the pTZ18R DNA, designated pX8 and pX10, were obtained following transformation of E. coli. Single-stranded DNAs were made from the subclones using the protocol provided by Pharmacia. The entire 1.4 kb Xba I fragments were sequenced. An additional 700 bases adjacent to the Xba I fragment was sequenced from the BamH I fragment in clone pB3 (fragment pB3 is in the same orientation as PX8) giving a total of 2123 bases of sequence (SEQ ID NO:1).

Example 2

Modification of the HSZ Gene by Site-Directed Mutagenesis

Three Nco I sites were present in the 1.4 kD Xba I fragment carrying the HSZ gene, all in the HSZ coding region. It was desirable to maintain only one of these sites (nucleotides 751–756 in SEQ ID NO:1) that included the translation start codon. Therefore, the Nco I sites at positions 870–875 and 1333–1338 were eliminated by oligonucleotide-directed site-specific mutagenesis [see Sambrook et al. (1989) Molecular Cloning: A Laboratory Manual, Cold Spring Harbor Laboratory Press]. The oligonucleotides synthesized for the mutagenesis were:
CFC99 ATGAACCCTT GGATGCA (SEQ ID NO:8)
CFC98 CCCACAGCAA TGGCGAT (SEQ ID NO:9)
Mutagenesis was carried out using a kit purchased from Bio-Rad (Richmond, Calif.), following the protocol provided by the vendor.

The process changed the A to T at 872 and the C to A at 1334. These were both at the third position of their respective codons and resulted in no change in the amino acid sequence encoded by the gene, with C̲ C̲ A̲ to C̲ C̲ T̲, still coding for Pro and C̲ C̲ C̲ to G̲ C̲ A̲, still coding for Ala. The plasmid clone containing the modified HSZ gene with a single Nco I site at the ATG start codon was designated pXBm. Because the native HSZ gene has a unique Xba I site at the stop codon of the gene (1384–1389, SEQ ID NO:1), a complete digest of the DNA with Nco I and Xba I yields a 637 bp fragment containing the entire coding sequence of the precursor HSZ polypeptide (SEQ ID NO:2).

It was desirable to create a form of the HSZ gene with alternative unique restriction endonuclease sites just past the end of the coding region. To do this oligonucleotides CFC104 (SEQ ID NO:10) and CFC105 (SEQ ID NO:11):
CFC104 5'-CTAGCCCGGGTAC-3' (SEQ ID NO:10)
CFC105 3'-GGGCCCATGGATC-5' (SEQ ID NO:11)
were annealed and ligated into the Xba I site, introducing two new restriction sites, Sma I and Kpn I, and destroying the Xba I site. The now unique Xba I site from nucleotide 1–6 in SEQ ID NO:1 and the Ssp I site from nucleotide 1823–1828 in SEQ ID NO:1 were used to obtain a fragment that included the HSZ coding region plus its 5' and 3' regulatory regions. This fragment was cloned into the commercially-available vector pTZ19R (Pharmacia) digested with Xba I and Sma I, yielding plasmid pCC10.

It was desirable to create an altered form of the HSZ gene with a unique restriction endonuclease site at the start of the mature protein, i.e. with the amino terminal signal sequence removed. To accomplish this a DNA fragment was generated using PCR as described in EXAMPLE 1. Template DNA for the PCR reaction was plasmid pX8m. Oligonucleotide primers for the reaction were:
CFC106 5'-CCACTTCA CCCATATCCCAGGGCACTT-3' (SEQ ID NO:12)
CFC88 5'-TTCTAT TGCAGCACCAACAAAGGG-3' (SEQ ID NO:13)
The CFC106 (SEQ ID NO:12) oligonucleotide provided the PCR-generated fragment with a BspH I site (underlined), which when digested with BspH I results in a cohesive-end identical to that generated by an Nco I digest. This site was located at the junction of the signal sequence and the mature HSZ coding sequence. The CFC88 (SEQ ID NO:13) oligonucleotide provided the PCR-generated fragment with an Xba I site (underlined) at the translation terminus of the HSZ gene. The BspH I-Xba I fragment (SEQ ID NO:3) obtained by digestion of the PCR-generated fragment, encodes the mature form of HSZ with the addition of a methionine residue at the amino terminus of the protein to permit initiation of translation.

Example 3

Expression of the HSZ Gene in E. coli

To express the HSZ coding sequence in *E. coli* the bacterial expression vector pBT430 was used. This vector is a derivative of pET-3a [Rosenberg et al. (1987) Gene 56:125–135] which employs the bacteriophage T7 RNA polymerase/T7 promoter system. Plasmid pBT430 was constructed by first destroying the EcoR I and Hind III sites in pET-3a at their original positions. An oligonucleotide adaptor containing EcoR I and Hind III sites was then inserted at the BamH I site of pET3a. This created pET-3aM with additional unique cloning sites for insertion of genes into the expression vector. Then, the Nde I site at the position of translation initiation was converted to an Nco I site using oligonucleotide-directed mutagenesis. The DNA sequence of pET-3aM in this region, 5'-CATATGG (Nde I site underlined), was converted to 5'-CCCATGG (Nco I site underlined) in pBT430.

The Nco I-Xba I fragment of pX8m (SEQ ID NO:2, see Example 2) was isolated from an agarose gel following electrophoresis using DEAE cellulose membrane as described in Example 1. This fragment was ligated to two annealed oligonucleotides, CFC104 (SEQ ID NO:10) and CFC105 (SEQ ID NO:11)
CFC104 5'-CTAGCCCGGGTAC-3' (SEQ ID NO:10)
CFC105 3'-GGGCCCATGGATC-5' (SEQ ID NO:11)
introducing two new restriction sites, Sma I and Kpn I at the Xba I end of the fragment. Ligation was terminated by heating at 65° C. for 10 minutes. The ligation products were digested Sma I, leaving a 3' blunt-ended fragment. Expression vector pBT430 was digested with EcoR I and the cohesive ends were filled in by addition of DATP, dTTP and the Klenow fragment of *E. coli* DNA polymerase. The blunt-ended vector DNA was then digested with Nco I and the reaction mixture was phenol-extracted and ethanol-precipitated twice. The 640 bp Nco I-Sma I fragment containing the HSZ coding region was ligated to the Nco I-blunt pBT430 vector. A clone containing a plasmid designated pCC11 was identified by screening *E. coli* transformants for the desired recombinant product. This plasmid was expected to express the precursor HSZ protein.

A plasmid designed to express the HSZ protein without its signal sequence in *E. coli* was also constructed. The mature HSZ encoding DNA fragment for this construction was generated using PCR with plasmid pX8m as template and oligonucleotides CFC106 (SEQ ID NO:12) and CFC88 (SEQ ID NO:13) as primers as described in Example 2:

and the ACC sequence following it codes for the threonine residue at the amino terminus of the mature protein. The Xba I site in the CFC88 (SEQ ID NO:13) oligonucleotide (underlined above) provided a convenient cloning site at the end of the coding sequence. The PCR reaction product was precipitated in 2M ammonium acetate, 70% ethanol two times to remove excess oligonucleotide primers. The ends of the DNA fragment were made blunt by react n with the Klenow fragment of *E. coli* DNA polymerase in the presence of all four deoxyribonucleotide triphosphates. The reaction products were separated by agarose gel electrophoresis and stained with ethidium bromide. The predominant 570 bp band was eluted using DEAE cellulose membrane as describe above. The DNA was then digested with BspH I, twice ethanol precipitated, and ligated to the same Nco I-blunt pBT430 expression vector fragment described above. A clone containing a plasmid designated pCC12 was identified by screening *E. coli* transformants for the desired recombinant product. The cloned PCRgenerated fragment was sequenced; the sequence was identical to SEQ ID NO:3.

To detect expression of the HSZ polypeptides plasmids pCC11 and pCC12 were transformed into *E. coli* strain HMS174 and an in vivo labelling experiment was performed as described by Studier and Moffatt (1986) J. Mol. Biol. 189:113–130. Proteins were labelled one hour after induction (by infection with λ phage CE6 carrying the T7 RNA polymerase gene) with $^{35}$S-methionine, which was expected to very prominently label these methionine rich polypeptides. Cell extracts were run on SDS polyacrylamide gels which were dried and autoradiographed. A prominent band of molecular weight about 20 kD was evident in both pCC11 and pCC12 extracts. This is the approximate size expected for the mature length HSZ polypeptide and suggested that the precursor protein made in the pCC11 transformant was being processed by *E. coli*. When total cell proteins were revealed by Coomassie brilliant blue staining following induction and SDS polyacrylamide gel electrophoresis, a prominent induced 20 kD protein was evident in the pCC12 lysates, but not in the pCC11 lysates.

Example 4

Purification of the HSZ protein produced in E. coli

A 1-L culture of *E. coli* strain BL21 (DE3) pLysE [Studier et al. (1990) Methods in Enzymology 185:60–89] transformed with pCC12 was grown in LB medium containing ampicillin (100 mg/L) and chloramphenicol (10 mg/L) at 37° C. At an optical density at 600 nm of 1.08, 1.2 mL of 0.1M IPTG (isopropylthio-β-galactoside, the inducer) was added and incubation was continued for 3 h at 37° C. The cells were collected by centrifugation, washed with 50 mM NaCl; 50 mM Tris-Cl, pH 7.5; 1 mM EDTA, resuspended with 10 mL of the same buffer, and frozen at −20° C.

```
CFC106  5'-CCACTTCATGACCCATATCCCAGGGCACTT-3'    (SEQ ID NO:12)
              MetThrHisIleProGlyHisLeu           (amino acids
                                                  1 to 8 of
                                                 SEQ ID NO:3)

CFC88   3'-GGGAAACAACCACGACGTAAGATCTATCTT-5'    (SEQ ID NO:13)
              ProPheValGlyAlaAlaPheEnd           (amino acids
                                                 185 to 191 of
                                                 SEQ ID NO:3)
```

The CFC106 (SEQ ID NO:12) oligonucleotide provided the PCR fragment with a BspH I site (underlined above) which generates cohesive ends identical to Nco I. The ATG sequence within the site is the translation initiation codon, The suspension was thawed and Triton X-100 was added to a concentration of 0.1%, followed by 3000 units of deoxyribonuclease I (Boehringer-Mannheim). After incubation at room temperature for 60 minutes the suspension was sonicated on ice to reduce viscosity. The mixture was centrifuged and the supernatant was discarded. The pellet was extracted twice with 5 mL of 70% isopropanol; 10 mM β-mercaptoethanol. HSZ, unlike most proteins, is soluble in this solvent. SDS polyacrylamide gel electrophoresis and Coomassie brilliant blue staining revealed that the HSZ protein was the major protein of the first extraction (>90%) and the only evident protein in the second extraction. Between 10 and 100 mg of HSZ protein were obtained from 1 L of cell culture. Purified HSZ protein was sent to Hazelton Research Facility, 310 Swampridge Road, Denver, PA 17517 to have rabbit antibodies raised against the protein.

Example 5

Construction of a Gene Encoding the High Methionine Domains of HSZ

Figure 3:
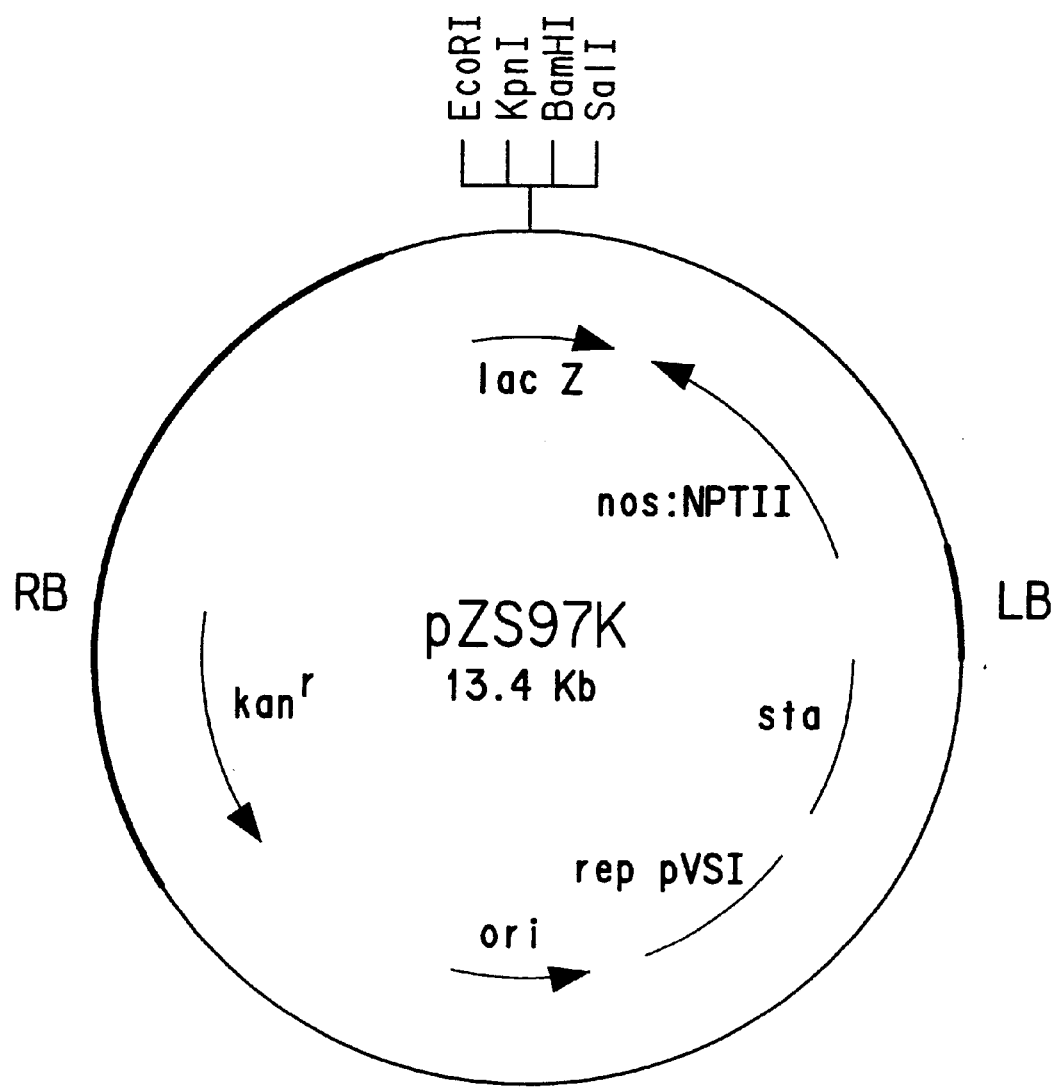
FIG. 3 shows a map of the binary plasmid vector pZS97K.

The HSZ protein is composed of a central very-methionine-rich region (approximately 48% methionine residues) flanked by amino terminal and carboxy terminal regions with lower methionine content (10% methionine and 7% methionine, respectively). The central region is composed of the repeating motif Met-Met-Met-Pro (SEQ ID NO:27). The related 10 kD zein protein has a similar structure (see FIG. 3). However, the central region of the HSZ protein is about twice as large as the corresponding region in the 10 kD zein, accounting for the increased methionine content of HSZ. The apparent duplication of the central high methionine domain in HSZ compared to 10 kD zein suggested that the central high methionine domain might have a stable structure and could be expressed by itself, yielding a very high methionine storage protein.

A gene was constructed to encode the high methionine domain (HMD) of HSZ. To accomplish this PCR was used as described in Example 1 with pX8 as the template DNA and the oligonucleotides JR5 (SEQ ID NO:14) and JR6 (SEQ ID NO:15) as primers for the DNA synthesis:

JR5 5'-TCACCGCTTCAGCAGTGC CCAATG-3' (SEQ ID NO:14)

JR6 5'-TCTTA TATGGCATCATCATTGGTGACACCATG CT-3' (SEQ ID NO:15)

Primer JR5 (SEQ ID NO:14) causes the addition of an Nde I site (underlined above) in the PCR product. Primer JR6 (SEQ ID NO:15) adds an EcoR I site (underlined above) in the PCR product. These sites permit ligation of the HMD to the pET-3aM expression vector [Rosenberg et al. (1987) Gene 56:125–135 and Example 3]. The ATG nucleotides of the Nde I site is the translation initiation codon in the expression vector and the EcoR I site immediately follows the translation termination codon.

The PCR product was digested with Nde I and EcoR I and ligated to pET-3aM which had been digested with Nde I and EcoR I. Following transformation of *E. coli*, clones containing the desired recombinant plasmid were identified and verified by DNA sequencing of the inserted DNA fragment. The nucleotide and derived amino acid sequence of the HMD gene is shown in SEQ ID NO:4.

Example 6

Construction of Chimeric Genes for Expression of HSZ in Plants

Three seed-specific gene expression cassettes were used for construction of chimeric genes for expression of HSZ in plants. The expression cassettes contained the regulatory regions from three highly expressed seed storage protein genes:

1) the β subunit of phaseolin from the bean Phaseolus vulgaris;
2) the α' subunit of β-conglycinin from soybean; and
3) the 10 kD zein from corn.

The cassettes are shown schematically in FIG. 2.

The phaseolin cassette includes about 500 nucleotides upstream (5') from the translation initiation codon and about 1650 nucleotides downstream (3') from the translation stop codon of phaseolin. Between the 5' and 3' regions are the unique restriction endonuclease sites Nco I (which includes the ATG translation initiation codon), Sma I, Kpn I and Xba I. The entire cassette is flanked by Hind III sites. The DNA sequence of these regulatory regions have been described in the literature [Doyle et al. (1986) J. Biol. Chem. 261:9228–9238]. Recent work by Bustos et al. [(1991) EMBO J. 10:1469–1479] indicates that the promoter region of this cassette does not include all of the DNA sequence elements required for the full expression level of the phaseolin promoter, but rather 20–30% of the full expression level would be expected.

The β-conglycinin cassette includes about 610 nucleotides upstream (5') from the translation initiation codon of β-conglycinin and about 1650 nucleotides downstream (3') from the translation stop codon of phaseolin. Between the 5' and 3' regions are the unique restriction endonuclease sites Nco I (which includes the ATG translation initiation codon), Sma I, Kpn I and Xba I. The entire cassette is flanked by Hind III sites. The DNA sequence of these regulatory regions have been described in the literature [Doyle et al. (1986) J. Biol. Chem. 261:9228–9238].

The 10 kD zein cassette includes about 925 nucleotides upstream (5') from the translation initiation codon and about 945 nucleotides downstream (3') from the translation stop codon of phaseolin. Between the 5' and 3' regions are the unique restriction endonuclease sites Nco I (which includes the ATG translation initiation codon) and Sma I. The entire cassette is flanked by an EcoR I site at the 5' end and BamH I, Sal I and Hind III sites at the 3' end. The DNA sequence of these regulatory regions have been described in the literature [Kirihara et al. (1988) Gene 71:359–370].

The Nco I-Xba I fragment containing the entire HSZ coding region (see Example 2) was isolated from an agarose gel following electrophoresis using DEAE cellulose membrane as described in Example 1. The BspH I-Xba I fragment containing the gene without the signal sequence, i.e. the mature protein coding sequence, was isolated as described in Example 3. These DNA fragments were inserted into the phaseolin and β-conglycinin expression cassettes which had been digested with Nco I-Xba I. Thus four chimeric genes were created:

1) phaseolin 5' region/native HSZ/phaseolin 3' region
2) phaseolin 5' region/mature HSZ/phaseolin 3' region
3) β-conglycinin 5' region/native HSZ/phaseolin 3' region
4) β-conglycinin 5' region/mature HSZ/phaseolin 3' region.

Additional chimeric genes were constructed to replace the native monocot signal sequence of HSZ with a dicot signal sequence from phaseolin. To do this ologonucleotides CFC 112 (SEQ ID NO:16) and CFC 113 (SEQ ID NO:17) were synthesized. The annealed oligonucleotides form an Nco I compatible end and an Nhe I/Spe I compatible end (see below).

```
CFC112 5'-CATGATGAGAGCAAGGGTTCCACTCCTGTTGCTGGGAATTCTT

CFC113 3'    TACTCTCGTTCCCAAGGTGAGGACAACGACCCTTAAGAA
             MetMetArgAlaArgValProLeuLeuLeuLeuGlyIleLeu

CFC112 TTCCTGGCATCACTTTCTGCTAGCTTTG        3'          (SEQ ID NO:16)

CFC113 AAGGACCGTAGTGAAAGACGATCGAAACGATC-5'             (SEQ ID NO:17)
       PheLeuAlaSerLeuSerAlaSerPhe                    (SEQ ID NO:16)
```

A plasmid, pCC13, containing the HSZ gene flanked by the phaseolin 5' and 3' regulatory regions was digested with Nco I and Spe I, removing most of the native signal sequence of HSZ. The annealled oligonucleotides, CFC112 (SEQ ID NO:16) and CFC113 (SEQ ID NO:17), were ligated to the digested pCC13. This plasmid thus created was designated pCC18 and the sequence of the chimeric gene containing the mature HSZ protein fused to the phaseolin signal sequence was confirmed by DNA sequencing (SEQ ID NO:18).

Because the Spe I site (nucleotides 57–62 in Seq ID NO:2) was not at the precise junction of the HSZ signal sequence/mature protein, two extra amino acids were added between the end of the phaseolin signal sequence and the mature HSZ protein by this procedure. In order to remove these an HSZ fragment was generated via PCR using the oligonucleotides CFC114 (SEQ ID NO:19, see below) and CFC 88 (SEQ ID NO:13, see EXAMPLE 2) serving as primers and with pCC18 as the DNA template.

```
CFC114
TTCTGCTAGC TTTGCTACCC ATATCCCAGG G (SEQ ID NO:19)
```

The PCR product was digested with Nhe I and Xba I and purified by gel electrophoresis. The plasmid pCC18 was digested with the same enzymes to remove the DNA fragment coding for the fusion protein containing the two extra amino acids and the PCR-generated DNA fragment was then inserted. The structure of the resultant plasmid, designated pCC24, was confirmed by DNA sequencing (SEQ ID NO:20).

In order to replace the native signal sequence of HSZ with the phaseolin signal sequence in the chimeric gene that contained the β-conglycinin 5' region, a PCR-generated fragment was synthesized using CFC123 (SEQ ID NO:21, see below) and CFC88 (SEQ ID NO:13, see EXAMPLE 2) as primers and pCC24 as template.

```
CFC123
ACTAATCATG ATGAGAGCAA GGGTTCCACT (SEQ ID NO:21)
```

The PCR-generated DNA fragment was digested with BspH I and Xba I and purified by gel electrophoresis. This DNA fragment was inserted into the β-conglycinin expression cassette which had been digested with Nco I-Xba I and the structure of the inserted fragment was confirmed by DNA sequencing (SEQ ID NO:20). This plasmid was designated pCC30.

The oligonucleotides CFC104 (SEQ ID NO:10) and CFC105 (SEQ ID NO:11) (see Example 3) were inserted into the 10 kD zein cassette at the Xba I site at the carboxy terminus adding a unique Sma I site. The Nco I-Sma I fragment containing the HSZ coding region was isolated from plasmid pCC10 (see Example 2) and inserted into Nco I-Sma I digested 10 kD zein cassette.

Example 7
Transformation of Tobacco with the Phaseolin-HSZ Chimeric Genes The phaseolin-HSZ chimeric gene cassettes, phaseolin 5' region/native HSZ/phaseolin 3' region, and phaseolin 5' region/mature HSZ/phaseolin 3' region (Example 6) were isolated as approximately 2.3 kb Hind III fragments. Hind III-BamH I adaptor oligonucleotides were added to these fragments for insertion into the unique BamH I site of the vector pZS97K (FIG. 3) which is part of a binary Ti plasmid vector system [Bevan, (1984) Nucl. Acids. Res. 12:8711–8720] of *Agrobacterium tumefaciens*. The vector contains: (1) the chimeric gene nopaline synthase/neomycin phosphotransferase (nos:NPT II) as a selectable marker for transformed plant cells [Bevan et al. (1983) Nature 304:184–186], (2) the left and right borders of the T-DNA of the Ti plasmid [Bevan (1984) Nucl. Acids. Res. 12:8711–8720], (3) the *E. coli* lacZ α-complementing segment [Vieria and Messing (1982) Gene 19:259–267] with unique restriction endonuclease sites for EcoR I, Kpn I, BamH I and Sal I, (4) the bacterial replication origin from the Pseudomonas plasmid pVS1 [Itoh et al. (1984) Plasmid 11:206–220], and (5) the bacterial neomycin phosphotransferase gene from Tn5 [Berg et al. (1975) Proc. Natl. Acad Sci. U.S.A. 72:3628–3632] as a selectable marker for transformed *A. tumefaciens*.

Figure 4:
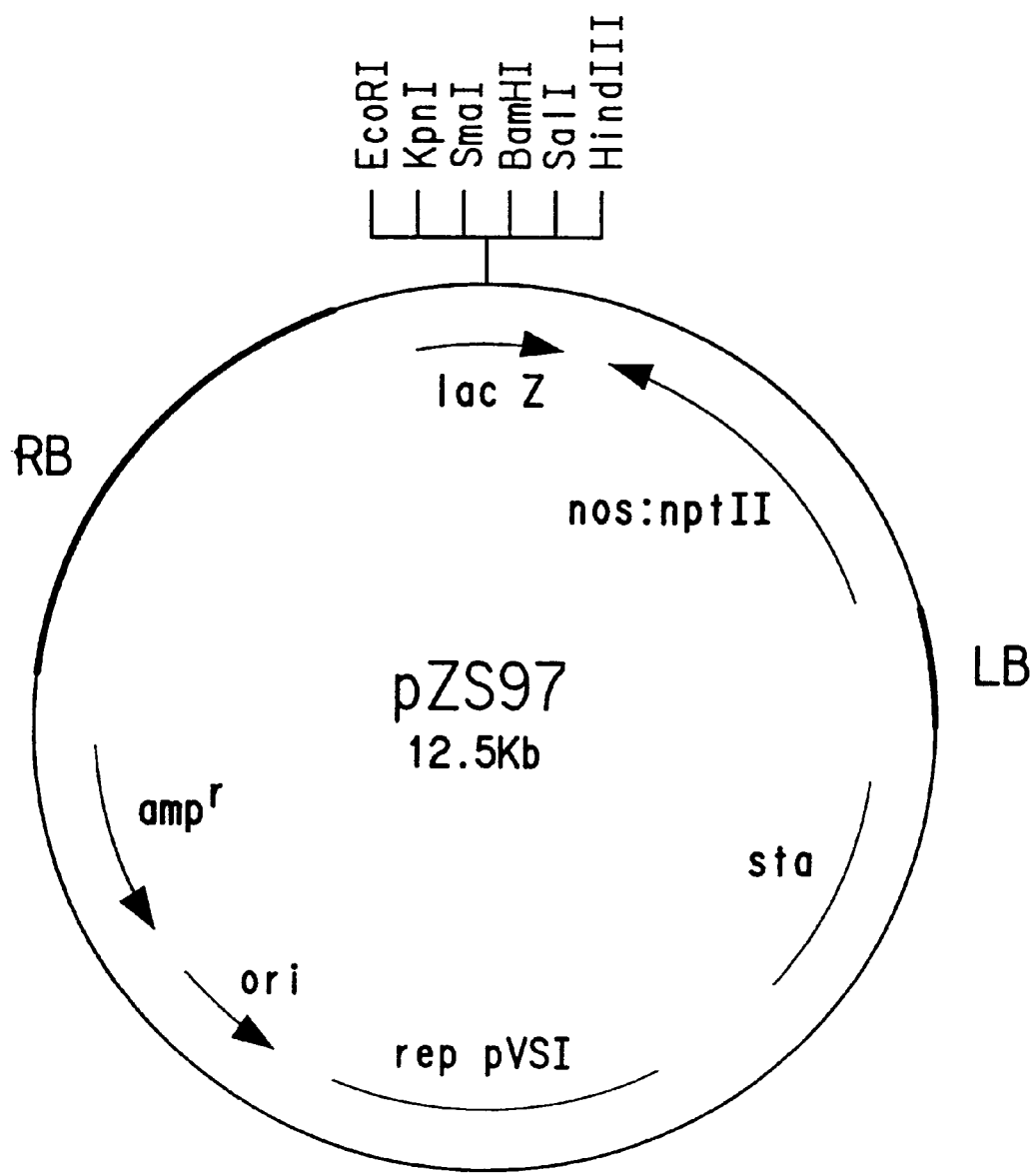
FIG. 4 shows a map of the binary plasmid vector pZS97.

The phaseolin-HSZ chimeric gene cassette, phaseolin 5' region/phaseolin signal sequence/mature HSZ/phaseolin 3' region, (Example 6) was isolated as an approximately 2.3 kb Hind III fragment. This fragment was inserted into the unique Hind III site of the binary vector pZS97 (FIG. 4). This vector is similar to pZS97K described above except for the presence of two additional unique cloning sites, Sma I and Hind III, and the bacterial β-lactamase gene (causing ampicillin resistance) as a selectable marker for transformed *A. tumefaciens* instead of the bacterial neomycin phosphotransferase gene.

The binary vectors containing the chimeric HSZ genes were transferred by tri-parental matings [Ruvkin et al. (1981) Nature 289:85–88] to Agrobacterium strain LBA4404/pAL4404 [Hockema et al. (1983) Nature 303:179–180]. The Agrobacterium transformants were used to inoculate tobacco leaf disks [Horsch et al. (1985) Science 227:1229–1231]. Transgenic plants were regenerated in selective medium containing kanamycin.

Genomic DNA was extracted from young leaves and analyzed using PCR to detect the presence of the chimeric HSZ genes in the transformed tobacco. The oligonucleotides CFC93 (SEQ ID NO:22, see below) and CFC77 (SEQ ID NO:7, see EXAMPLE 1) were used as primers for the PCR reaction.

```
CFC93
GAATGCAGCA CCAACAAAGG GTTGCTGTAA (SEQ ID NO:22)
```

These primers would be expected to generate a 425 bp DNA fragment internal to the HSZ gene. Sixteen of twenty transformants tested were positive in this assay (see Tables 1 and 2).

To assay for expression of the chimeric genes the transformed plants were allowed to flower, self-pollinate and go to seed. Total proteins were extracted from mature seeds as follows. Approximately 200 mg of seeds were put into a 1.5 mL disposable plastic microfuge tube and ground in 0.25 mL of 50 mM Tris-Cl pH 6.8, 2 mM EDTA, 1% SDS, 1% β-mercaptoethanol. The grinding was done using a motorized grinder with disposable plastic shafts designed to fit into the microfuge tube. The resultant suspensions were centrifuged for 5 minutes at room temperature in a microfuge to remove particulates. Total protein contents of the supernatants were assayed using the BioRad protein assay with bovine serum albumin as a standard.

From each extract 10 μg of protein was run per lane on an SDS polyacrylamide gel, with bacterially produced mature HSZ serving as a positive control and protein extracted from untransformed tobacco seeds serving as a negative control. The proteins were then electrophoretically blotted onto a nitrocellulose membrane. The membranes were exposed to HSZ antibodies (see EXAMPLE 4) at a 1:700 dilution of the rabbit serum using standard protocol provided by BioRad with their Immun-Blot Kit. Following rinsing to remove unbound primary antibody the membranes were exposed to the secondary antibody, donkey anti-rabbit Ig conjugated to horseradish peroxidase (Amersham) at a 1:3000 dilution. Following rinsing to remove unbound secondary antibody the membranes were exposed to Amersham chemiluminescence reagent and X-ray film.

Most of the transformants that contained the HSZ gene based on the PCR analysis also produced HSZ protein based on the immunological screening (Tables 1–3). In all cases the size of the protein produced was approximately equal to mature HSZ produced in *E. coli*, indicating that both the native and the phaseolin signal sequence had been removed, and thus suggesting that the protein had entered the endoplasmic reticulum.

Seeds were also extracted with 70% isopropanol/1% β-mercaptoethanol, a solvent in which few proteins other than HSZ are soluble. The proteins were then subjected to SDS-PAGE, Western blotting, and immunological probing as described above. Under these conditions a protein the size of mature HSZ was again observed, confirming the identity of the detected proteins as HSZ.

The level of expression of HSZ in the transformed lines was estimated based on the sensitivity of the HSZ antibody and the amount of protein loaded on the SDS-PAGE gel. HSZ ranged from about 0.05–0.5% of the total seed protein.

To measure the amino acid composition of the seeds, 6 seeds were hydrolyzed in 6 N hydrochloric acid, 0.4% β-mercaptoethanol under nitrogen for 24 hours at 110–120° C.; 1/10 of the sample was run on a Beckman Model 6300 amino acid analyzer using post-column ninhydrin detection. Relative methionine levels in the seeds were compared as a methionine:leucine ratio, thus using leucine as an internal standard. There was about a 6% standard deviation in the methionine:leucine ratio. At the highest level of expression of HSZ determined by the Western blot analysis, HSZ would be expected to increase the level of methionine in the seed by about 10%. Because this was so close to the standard deviation, no effect of the expression of HSZ on the total seed methionine was observed (Tables 1–3).

TABLE 1 pCC15 transformants phaseolin 5'/mature HSZ/phaseolin 3'

| LINE | PCR | Western | Met:Leu |
|---|---|---|---|
| 15-17A | + | + | |
| 15-29A | + | − | |
| 15-34A | + | + | |

TABLE 1-continued pCC15 transformants phaseolin 5'/mature HSZ/phaseolin 3'

| LINE | PCR | Western | Met:Leu |
|---|---|---|---|
| 15-40A | + | + | 0.19 |
| 15-50A | + | +++ | 0.19 |
| 15-55A | + | ++ | |
| 15-27B | + | + | |
| 15-49B | − | + | |
| 15-54B | + | − | |
| 15-38A | + | + | |

TABLE 2 pCC16 transformants phaseolin 5'/native HSZ/phaseolin 3'

| LINE | PCR | Western | Met:Leu |
|---|---|---|---|
| 16-7A | + | +++ | 0.20 |
| 16-16A | + | + | |
| 16-24A | − | − | |
| 16-48A | − | − | |
| 16-6B | + | − | |
| 16-11B | − | − | 0.19 |
| 16-33B | + | + | |
| 16-49B | + | − | |
| 16-54B | + | − | |
| 16-55B | + | − | |

TABLE 3 pCC36 transformants phaseolin 5'/phaseolin ss/mature HSZ/phaseolin 3'

| LINE | PCR | Western | Met:Leu |
|---|---|---|---|
| 36-1B | | + | |
| 36-4B | | + | |
| 36-5A | | + | |
| 36-20A | | +++ | 0.20 |
| 36-23C | | + | |
| 36-35B | | ++ | |
| 36-39A | | + | |
| 36-46B | | ++ | |
| 36-47D | | − | |
| 36-55D | | − | |

Example 8

Expression of the HMD protein in *E. coli*

A culture of *E. coli* strain BL21 (DE3) pLysE [Studier et al. (1990) Methods in Enzymology 185:60–89] transformed with plasmid pX8M-18 was grown in 10 L LB medium containing ampicillin (100 mg/L) at 37° C. At an optical density at 600 nm of about 1, IPTG (isopropylthio-β-galactoside, the inducer) was added to a final concentration of 1 mM and incubation was continued for 8 h at 37° C. The cells were collected by centrifugation, washed with 50 mM NaCl, 50 mM Tris-Cl, (pH 7.5), 1 mM EDTA (buffer A), and frozen at −80° C.

The frozen cells were thawed on ice in 5 mL of buffer A/gram cells. Deoxyribonuclease I (Sigma) was added to a concentration of 0.1 mg/mL. After incubation at room temperature for 60 minutes the suspension was sonicated on ice to reduce viscosity. The mixture was centrifuged and the supernatant was discarded. The pellet was extracted twice with 25 mL of 70% isopropanol, 10 mM β-mercaptoethanol. HMD, like HSZ, is soluble in this solvent. SDS polyacrylamide gel electrophoresis and Coomassie brilliant blue staining revealed that the HMD protein was the major protein of the extraction. Western blot analysis demonstrated that HMD protein cross-reacted with rabbit antibody raised to HSZ.

Example 9

Transformation of Tobacco with the β-conalycinin-HSZ Chimeric Genes

The β-conglycinin chimeric gene cassettes, β-conglycinin 5' region/native HSZ/phaseolin 3' region, β-conglycinin 5' region/mature HSZ/phaseolin 3' region, and β-conglycinin 5' region/phaseolin signal sequence/mature HSZ/phaseolin 3' region (Example 6) were isolated as approximately 2.4 kb Hind III fragments. These fragments were inserted into the unique Hind III site of the binary vector pZS97 (FIG. 4). This vector is similar to pZS97K described in EXAMPLE 7 except for the presence of two additional unique cloning sites, Sma I and Hind III, and the bacterial β-lactamase gene (causing ampicillin resistance) as a selectable marker for transformed A. tumefaciens instead of the bacterial neomycin phosphotransferase gene.

The binary vectors containing the chimeric HSZ genes were transferred by tri-parental matings [Ruvkin et al. (1981) Nature 289:85–88] to Agrobacterium strain LBA4404/pAL4404 [Hockema et al (1983), Nature 303:179–180]. The Agrobacterium transformants were used to inoculate tobacco leaf disks [Horsch et al. (1985) Science 227:1229–1231]. Transgenic plants were regenerated in selective medium containing kanamycin.

To assay for expression of the chimeric genes the transformed plants were allowed to flower, self-pollinate and go to seed. Total proteins were extracted from mature seeds as follows. Approximately 200 mg of seeds were put into a 1.5 mL disposable plastic microfuge tube and ground in 0.25 mL of 50 mM Tris-Cl pH 6.8, 2 mM EDTA, 1% SDS, 1% β-mercaptoethanol. The grinding was done using a motorized grinder with disposable plastic shafts designed to fit into the microfuge tube. The resultant suspensions were centrifuged for 5 minutes at room temperature in a microfuge to remove particulates. Total protein contents of the supernatants were assayed using the BioRad protein assay with bovine serum albumin as a standard.

From each extract 10 μg of protein was run per lane on an SDS polyacrylamide gel, with bacterially produced mature HSZ serving as a positive control and protein extracted from untransformed tobacco seeds serving as a negative control. The proteins were then electrophoretically blotted onto a nitrocellulose membrane. The membranes were exposed to HSZ antibodies (see EXAMPLE 4) at a 1:700 dilution of the rabbit serum using standard protocol provided by BioRad with their Immun-Blot Kit. Following rinsing to remove unbound primary antibody the membranes were exposed to the secondary antibody, donkey anti-rabbit Ig conjugated to horseradish peroxidase (Amersham) at a 1:3000 dilution. Following rinsing to remove unbound secondary antibody the membranes were exposed to Amersham chemiluminescence reagent and X-ray film.

One transformant containing the chimeric gene β-conglycinin 5' region/mature HSZ/phaseolin 3' region and two transformants containing the chimeric gene β-conglycinin 5' region/native HSZ/phaseolin 3' region each produced HSZ protein. Four of seven transformants containing the chimeric gene β-conglycinin 5' region/phaseolin signal sequence-mature HSZ/phaseolin 3' region produced HSZ protein (Table 4). In all cases the size of the protein produced was approximately equal to mature HSZ produced in E. coli, indicating that both the native and the phaseolin signal sequence had been removed, and thus suggesting that the protein had entered the endoplasmic reticulum.

To measure the amino acid composition of the seeds, 6 seeds were hydrolyzed in 6N hydrochloric acid, 0.4% β-mercaptoethanol under nitrogen for 24 hours at 110–120° C.; 1/10 of the sample was run on a Beckman Model 6300 amino acid analyzer using post-column ninhydrin detection. Relative methionine levels in the seeds were compared as a methionine:leucine ratio, thus using leucine as an internal standard. There was about a 5% standard deviation in the methionine:leucine ratio. The line with the highest level of HSZ expression based on the Western blot analysis had the highest total seed methionine observed (Table 4), but this was only about 7% above the mean. While this is too close to the error in the measurement to be certain, it is likely that this high methionine level is due to the expression of HSZ.

TABLE 4

| pCC39 transformants β-conglycinin 5'/ phaseolin signal sequence-mature HSZ/phaseolin 3' | | |
|---|---|---|
| LINE | Western | Met:Leu |
| 39-1C | + | 0.20 |
| 39-9C | − | 0.20 |
| 39-13A | − | 0.21 |
| 39-14C | + | 0.20 |
| 39-15C | − | 0.20 |
| 39-28A | ++ | 0.21 |
| 39-36A | + | 0.20 |

Example 10

Construction of Chimeric Gene for Expression of HMD in Plants

As in EXAMPLE 6, a seed-specific gene expression cassette was used for construction of a chimeric gene for expression of HMD in plants. The expression cassette contained the regulatory region from the β-subunit of phaseolin from the bean Phaseolus vulgaris. The chimeric gene created also contained a dicot signal sequence from phaseolin: phaseolin 5' region/phaseolin signal sequence/HMD/phaseolin 3' region PCR primers, CLM 1 (SEQ ID NO:23) and CLM 2 (SEQ ID NO:24) (see below) were synthesized and used with the plasmid pJRHMD1 as template to generate a DNA fragment containing the HMD sequence fused to the 3' end of the phaseolin signal sequence and flanked by NheI and XbaI sites. The plasmid pCC24, discussed in EXAMPLE 6, was digested with NheI, which cuts within the phaseolin signal sequence, and XbaI and purified by agarose gel electrophoresis. The purified vector was ligated to the PCR product formed from CLM 1 (SEQ ID NO:23), CLM 2 (SEQ ID NO:24) and pJRHMD1, thus regenerating the complete phaseolin signal sequence linked to HMD. The ligation product was designated pJRHMD2 and the sequence of the chimeric gene (SEQ ID NO:25) was confirmed by DNA sequencing.

```
CLM 1      NheI
5'      TGCTTGCTAGCTTTGCTATGCCAATGATGATGCCGGGT 3'        (SEQ ID NO:23)
            AlaSerPheAlaMetProMetMetMetProGly

CLM 2      XbaI
5'      TGCTTTCTAGACTATGGCATCATCATTGGTGACACC    3'        (SEQ ID NO:24)
```

Example 11

Transformation of Soybean with a Phaseolin-HSZ Chimeric Gene

To induce somatic embryos, cotyledons, 4–5 mm in length dissected from surface sterilized, immature seeds of the soybean cultivar XP3015, were cultured in the dark at 25° C. on an agar medium (SB1 or SB2) for 8–10 weeks. Somatic embryos, which produced secondary embryos were excised and placed into a liquid medium (SB55). After repeated selection for clusters of somatic embryos which multiplied as early, globular staged embryos, the suspensions were maintained as described below.

Soybean embryogenic suspension cultures were maintained in 35 mL liquid media (SB55) on a rotary shaker, 150 rpm, at 28° C. with mixed florescent and incandescent lights on a 16:8 hour day/night schedule. Cultures were subcultured every four weeks by inoculating approximately 35 mg of tissue into 35 mL of liquid medium.

Soybean embryogenic suspension cultures were transformed by the method of particle gun bombardment (Kline et al. (1987) Nature (London) 327:70, U.S. Pat. No. 4,945, 050). A Du Pont Biolistic® PDS1000/HE instrument (helium retrofit) was used for these transformations.

The plasmid vector used for transformation was a derivative of pGEM9Z (Promega Biological Research Products). As a selectable marker a chimeric gene composed of the 35S promoter from Cauliflower Mosaic Virus [Odell et al.(1985) Nature 313:810–812], the hygromycin phosphotransferase gene from plasmid pJR225 (from $E.$ $coli$) [Gritz et al.(1983) Gene 25:179–188] and the 3' region of the nopaline synthase gene from the T-DNA of the Ti plasmid of $Agrobacterium$ $tumefaciens$ (SEQ ID NO:26) was at the Sal I site of the vector. The phaseolin-HSZ chimeric gene cassette, phaseolin 5' region/phaseolin signal sequence/mature HSZ/ phaseolin 3' region, (Example 6) was isolated as an approximately 2.3 kb Hind III fragment. This fragment was inserted into the unique Hind III site of the vector.

To 50 μL of a 60 mg/mL 1 μm gold particle suspension was added (in order); 5 μL DNA(1 μg/μL), 20 μl spermidine (0.1M), and 50 μL CaCl$_2$ (2.5M). The particle preparation was agitated for three minutes, spun in a microfuge for 10 seconds and the supernatant removed. The DNA-coated particles were then washed once in 400 μL 70% ethanol and resuspended in 40 μL of anhydrous ethanol. The DNA/ particle suspension was sonicated three times for one second each. Five μL of the DNA-coated gold particles were then loaded on each macro carrier disk.

Approximately 300–400 mg of a four-week-old suspension culture was placed in an empty 60×15 mm petri dish and the residual liquid removed from the tissue with a pipette. For each transformation experiment, approximately 5–10 plates of tissue are normally bombarded. Membrane rupture pressure was set at 1000 psi and the chamber was evacuated to a vacuum of 28 inches mercury. The tissue was placed approximately 3.5 inches away from the retaining screen and bombarded three times. Following bombardment, the tissue was placed back into liquid and cultured as described above.

Seven days post bombardment, the liquid media was exchanged with fresh SB55 containing 50 mg/mL hygromycin. The selective media was refreshed weekly. Seven weeks post bombardment, green, transformed tissue was observed growing from untransformed, necrotic embryogenic clusters. Isolated green tissue was removed and inoculated into individual flasks to generate new, clonally propagated, transformed embryogenic suspension cultures. Thus each new line was treated as an independent transformation event. These suspensions could then be subcultured and maintained as clusters of immature embryos or regenerated into whole plants by maturation and germination of individual somatic embryos.

Transformed embryogenic clusters were removed from liquid culture and placed on a solid agar media (SB103) containing no hormones or antibiotics. Embryos were cultured for eight weeks at 26° C. with mixed florescent and incandescent lights on a 16:8 hour day/night schedule During this period, individual embryos were removed from the clusters and analyzed for production of the HSZ protein as described below. After eight weeks, the embryos are suitable for germination.

Individual embryos were frozen in liquid nitrogen, and ground to a fine powder with a morter and pestle prechilled in liquid nitrogen. The powder was scraped into an eppendorf centrifuge tube and extracted twice with hexane at room temperature. The residue was incubated at 60° C. for 30 min to allow residual hexane to evaporate. Then 100 μL of 50 mM Tris-HCl pH6.7, 2 mM EDTA, 1% SDS 1% β-mercaptoethanol (TESβ) was added to the pellet and it was ground at low speed for about 10 sec using a motorized grinder with disposable plastic shafts designed to fit into the microfuge tube. The resultant suspensions were centrifuged for 5 min at room temperature in a microfuge and the supernatant was removed and saved. The pellet was resuspended in 50 μL of 70% isopropanol, 10 mM β-mercaptoethanol by grinding as above. The tube was incubated at 60° C. for 5 min and centrifuged as above. The supernatant was saved and the pellet extracted again with 50 μL of 70% isopropanol, 10 mM β-mercaptoethanol. The alcohol extracts were pooled and lyophilized; the residue was then resuspended in 50 μL of TESβ. This sample and the first TESβ extract were assayed for the presence of HSZ protein by Western blot as described in Example 9. Two of three transformed lines tested showed expression of HSZ protein.

Media:
SB55 Stock Solutions (grams per liter):

| MS Sulfate 100X Stock | | MS Halides 100X Stock | |
|---|---|---|---|
| MgSO$_4$ 7H$_2$O | 37.0, | CaCl$_2$ 2H$_2$O | 44.0, |
| MnSO$_4$ H$_2$O | 1.69, | KI | 0.083, |
| ZnSO$_4$ 7H$_2$O | 0.86, | CoCl$_2$ 6H$_2$O | 0.00125 |
| CuSO$_4$ 5H$_2$O | 0.0025 | | |

-continued

Media:
SB55 Stock Solutions (grams per liter):

| MS P,B,Mo 100X Stock | | MS FeEDTA 100X Stock | |
|---|---|---|---|
| KH$_2$PO$_4$ | 17.0, | Na$_2$EDTA | 3.724, |
| H$_3$BO$_3$ | 0.62, | FeSO$_4$ 7H$_2$O | 2.784 |
| Na$_2$MoO$_4$ 2H$_2$O | 0.025 | | |
| B5 Vitamin Stock | | SB55 (per liter) | |
| 10 g m-inositol, | | 10 mL each MS stocks, | |
| 100 mg nicotinic acid, | | 1 mL B5 Vitamin stock | |
| 100 mg pyridoxine HCl, | | 0.8 g NH$_4$NO$_3$ | |
| 1 g thiamine | | 3.033 g KNO$_3$ | |
| | | 1 mL 2,4-D (10 mg/mL stock) | |
| | | 60 g sucrose | |
| | | 0.667 g asparagine | |
| | | pH 5.7 | |
| SB103 (per liter) | | SB1 (per liter) | |
| MS Salts | | MS Salts | |
| 6% maltose | | B5 Vitamins | |
| 750 mg MgCl$_2$ | | 0.175M glucose | |
| 0.2% Gelrite | | 20 mg 2,4-D | |
| pH 5.7 | | 0.8% agar | |
| | | pH 5.8 | |
| SB2 | | | |
| same as SB1 except 40 mg/L 2,4-D | | | |

Example 12

Transformation of Maize with a High-Sulfur Storage Protein Gene

Callus cultures were initiated from immature embryos (about 1.5 to 2.0 mm) dissected from kernels derived from crosses of the genotypes A188 and B73 10 to 12 days after pollination. The embryos were placed with the axis-side facing down and in contact with agarose-solidified N6 medium. The embryos were kept in the dark at 27° C. Friable embryogenic callus consisting of undifferentiated masses of cells with somatic proembryoids and embryoids borne on suspensor structures proliferates from the scutellum of these immature embryos. The embryogenic callus isolated from the primary explant was cultured on N6 medium and sub-cultured on this medium every 2 to 3 weeks.

The particle bombardment method was used to transfer genes to the callus culture cells. A Biolistic® PDS-1000/He (BioRAD Laboratories, Hercules, Calif.) was used for these experiments.

A plasmid vector containing a selectable marker gene was used in the transformations. The plasmid, pALSLUC [Fromm et al. (1990) Biotechnology 8:833–839], contains a cDNA of the maize acetolactate synthase (ALS) gene. The ALS cDNA had been mutated in vitro so that the enzyme coded by the gene would be resistant to chlorsulfuron. The change consisted of mutating a tryptophan codon at position 1626 of the cDNA to a leucine codon. The ALS gene is under the control of the 35S promoter from Cauliflower Mosaic Virus [Odell et al., (1985) Nature 313:810–812] and the 3U region of the nopaline synthase gene from the T-DNA of the Ti plasmid of Agrobacterium tumefaciens. This plasmid also contains a gene that uses the 35S promoter from Cauliflower Mosaic Virus and the 3U region of the nopaline synthase gene to express a firefly luciferase coding region [de Wet et al. (1987) Molec. Cell Biol. 7:725–737]. The chimeric HSZ gene was delivered on a second plasmid. This plasmid (pCC21, see EXAMPLE 6) contains the HSZ coding region under the control of the promoter region and the 3U end from the gene that codes for the 10 kd storage protein gene from maize [Kirihara et al. (1988) Gene 71:359–370].

These plasmids (pALSLUC and pCC21) were co-precipitated onto the surface of gold particles. To accomplish this 5 μg of pALSLUC and 2 μg of pCC21 (each in Tris-EDTA buffer at a concentration of about 1 μg/μL) were added to 50 μL of gold particles (average diameter of 1 5 m) suspended in water (60 mg of gold per mL). Calcium chloride (50 μL of a 2.5M solution) and spermidine (20 μL of a 1.0M solution) were then added to the gold-DNA suspension as the tube was vortexing. The particles were then centrifuged in a microfuge for 10 seconds and the supernatant removed. The particles were then resuspended in 200 μL of absolute ethanol. The particles were centrifuged again and the supernatant removed. The particles were then resuspended in 30 μL of ethanol. Five μL of the DNA-coated gold particles were then loaded on each macro carrier disk.

Small clusters (2 to 3 mm in diameter) of embryogenic callus was arranged on the surface of agarose-solidified N6 medium contained in a petri dish 12 cm in diameter. The tissue covered a circular area of about 6 cm in diameter. The petri dish containing the tissue was placed in the chamber of the PDS-1000/He. The air in the chamber was then evacuated to a vacuum of 28 inch of Hg. The macrocarrier was accelerated with a helium shock wave using a rupture membrane that bursts when the He pressure in the shock tube reaches 1000 psi. The tissue was placed approximately 8 cm from the stopping screen. Ten plates of tissue were bombarded with the DNA-coated gold particles.

Seven days after bombardment the tissue was transferred to N6 medium that contained chlorsulfuron (50 nM) and lacked casein or proline. The tissue continued to grow slowly on this medium. After an additional 2 weeks the tissue was transferred to fresh N6 medium containing chlorsulfuron. After 8 weeks an area of about 1 cm in diameter of actively growing callus was identified on one of the plates containing chlorsulfuron-supplemented medium. This callus continued to grow when sub-cultured on the selective medium. Some of this callus has been transferred to medium that allows plant regeneration.

Luciferase activity was measured in this callus. Untransformed callus tissue has luciferase activity of about 500 light units per mg of fresh tissue. The callus that grew on chlorsulfuron had luciferase activity of about 20,000 light units per mg of fresh tissue. This result indicates that genes from pALSLUC are expressed in this callus line. Southern analysis was performed for the presence of both the introduced ALS gene and the introduced chimeric storage protein gene. Both introduced genes were observed by Southern analysis.

For analysis of the HSZ gene, genomic DNA from the transformed callus line (Tx-X8A) or callus derived from the same genotype but that was not transformed (AB91) was digested with either Xba I or EcoR I. The digested DNA was fractionated by gel electrophoresis through agarose and transferred to a nylon membrane using standard techniques.

The nylon blot was hybridized to a probe prepared from a part of the HSZ coding region. AB91 callus exhibited one dominant band that corresponds to the native HSZ gene. An additional band of higher molecular weight was found in the Tx-X8A callus. This band corresponds to the introduced chimeric HSZ gene.

N6 Medium

| Component | Quantity per liter | Component | Quantity per liter |
|---|---|---|---|
| Solution I | | Solution I | |
| $CaCl_2$ (1M) | 10.0 mL | $(NH_4)_2SO_4$ | 23.0 g |
| Solution III | 1.25 mL | $KNO_3$ | 141.5 g |
| $MgSO_4$ (1M) | 10.0 mL | $KH_2PO_4$ | 20.0 g |
| Solution V | 0.75 mL | $H_2O$ | 500.0 mL |
| Vitamin Stock | 1.0 mL | | |
| Casein hydrolysate | 1.0 mL | Vitamin Stock | |
| Sucrose | 0.1 g | niacin | 0.13 g |
| Myo-inositol | 60.0 g | thiamine | 0.025 g |

-continued

N6 Medium

| Component | Quantity per liter | Component | Quantity per liter |
|---|---|---|---|
| 2,4-D (2 mg/mL stock) | 0.1 g | pyridoxine | 0.025 g |
| pH to 5.8 | 0.5 mL | calcium pantothenate | 0.025 g |
| Add 6g of agarose for plates | | $H_2O$ | 100.0 mL |
| Solution III | | Solution V | |
| $Na_2EDTA$ | 1.85 g | $H_3BO_3$ | 0.16 g |
| $FeSO_4.7H_2O$ | 1.35 g | $MnSO_4.H_2O$ | 0.33 g |
| $H_2O$ | 500.0 mL | $ZnSO_4.7H_2O$ | 0.15 g |
| | | KI | 0.08 g |
| | | $Na_2MoO_4.2H_2O$ | 0.025 g |
| | | $CuSO_4.5H_2O$ | 0.0025 g |
| | | $CoCl_2.2H_2O$ | 0.0025 g |
| | | $H_2O$ | 100.0 mL |

What is claimed is:

1. An isolated and purified nucleic acid fragment comprising a nucleotide sequence encoding the amino acid sequence set forth in SEQ ID NO:2, and designated "HSZ corn seed storage protein" or an amino acid sequence essentially similar to it in that:

(a) the encoded protein contains a central region of about 93 amino acids which region contains about 45 methionine residues;

(b) the mature form of the encoded protein, by molar ratio, contains about 28% methionine;

(c) the encoded protein contains a signal peptide capable of causing the protein to be transported into the endoplasmic reticulum wherein the signal peptide is located at an amino end of the encoded protein;

(d) the encoded protein contains a sequence of about 53 amino acids having about 7 sulfur containing amino acids, about 6 proline residues, and about 16 amino acids selected from the group consisting of glycine, alanine, valine, leucine and isoleucine, further wherein said sequence is located between the signal peptide and central region; and (e) the encoded protein contains a sequence of about 44 amino acids having about 4 sulfur-containing amino acids, about 6 proline residues, and about 14 amino acids selected from the group consisting of glycine, alanine, valine, leucine and isoleucine, further wherein said sequence is located between the central region and carboxyl end.

2. An isolated and purified nucleic acid fragment comprising a nucleotide sequence encoding the amino acid sequence set forth in SEQ ID NO:3, and designated "mature HSZ corn seed storage protein" or an amino acid sequence essentially similar to it in that:

(a) the encoded protein contains a central region of about 93 amino acids which region contains about 45 methionine residues;

(b) the mature form of the encoded protein, by molar ratio, contains about 28% methionine;

(c) the encoded protein contains a sequence of about 53 amino acids having about 7 sulfur containing amino acids, about 6 proline residues, and about 16 amino acids selected from the group consisting of glycine, alanine, valine, leucine and isoleucine, further wherein said sequence is located between the amino terminal end and the central region; and (d) the encoded protein contains a sequence of about 44 amino acids having about 4 sulfur-containing amino acids, about 6 proline residues, and about 14 amino acids selected from the group consisting of glycine, alanine, valine, leucine and isoleucine, further wherein said sequence is located between the central region and carboxyl end.

3. An isolated and purified nucleic acid fragment comprising a nucleotide sequence encoding the amino acid sequence set forth in SEQ ID NO:4, and designated "HMD corn seed storage protein" or an amino acid sequence essentially similar to it, in that;

(a) the encoded protein is about 93 amino acids of which about 45 are methionine residues; and (b) the encoded protein, by molar ratio, contains about 28% methionine.

4. The nucleic acid fragment of claim 2 operably linked to a signal sequence from a dirotyledonous plant.

5. The nucleic acid fragment of claim 3 operably linked to a plant signal sequence.

6. A chimeric gene comprising the nucleic acid fragment of any of claims 1–5 operably linked to a regulatory sequence directing expression in one or more organs of a plant.

7. The chimeric gene of claim 6 wherein the regulatory sequence is a seed-specific regulatory sequence.

8. A plant transformed with the chimeric gene of claim 6.

9. A plant according to claim 8 wherein the plant is selected from the group consisting of corn, soybean, canola, tobacco, and rice.

10. Seeds obtained from the plant of claim 8 which comprise the chimeric gene of claim 6.

11. A chimeric gene comprising the nucleic acid fragment of claims 2 or 3 operably linked to a regulatory sequence directing expression in microorganisms.

12. A microorganism transformed with the chimeric gene of claim 11.

13. A polypeptide product of the expression in a procaryotic or eucaryotic host cell of a nucleic acid fragment according to claims 1, 2 or 3.

14. A plant containing the polypeptide product of claim 13.

15. A seed containing the polypeptide product of claim 13.

16. A method for increasing the methionine content of plants comprising:

(a) transforming a plant cell with the chimeric gene of claim 6;

(b) growing fertile, sexually mature plants from said transformed plant cell; and (c) selecting progeny seed from said fertile plants for increased levels of methionine relative to untransformed plant cells.

17. A method for producing protein rich in methionine in a microorganism comprising:
(a) transforming a microorganism with the chimeric gene of claim 11;
(b) growing said microorganism under conditions for expression of protein rich in methionine; and
(c) isolating the protein from the microorganism of step (b).

18. Essentially pure plasmid pCC10 identified by the deposit accession number ATCC 68490.

19. The chimeric gene of claim 6 operably linked to a nucleic acid fragment encoding an intracellular targeting signal.

* * * * *

```
                          SEQUENCE LISTING (1) GENERAL INFORMATION:

(iii) NUMBER OF SEQUENCES:28

(2) INFORMATION FOR SEQ ID NO:1:

(i) SEQUENCE CHARACTERISTICS:
          (A) LENGTH:  2123 nucleotides (B) TYPE: Nucleic Acid (C) STRANDEDNESS:  single (D) TOPOLOGY:  linear (ii) MOLECULE TYPE:  genomic DNA (iii) HYPOTHETICAL:  NO (iv) ANTI-SENSE:  NO (v) FRAGMENT TYPE:

(vi) ORIGINAL SOURCE:
          (A) ORGANISM:  Zea mays L (B) STRAIN:  unknown (C) CELL TYPE:  unknown (vii) IMMEDIATE SOURCE:
          (A) LIBRARY: maize genomic library obtained from Clontech
          (B) CLONE:  X8

(viii) POSITION IN GENOME:  unknown
```

(x) PUBLICATION INFORMATION: unpublished sequence (xi) SEQUENCE DESCRIPTION: SEQ ID NO:1:

```
TCTAGAGCCT ATTACCATCT CTACTCACGG GTCGTAGAGG TGGTGAGGTA            50

GGCTACAGCT GGTGACAATC CTACTCACCC TTTGTAATCC TCTACGGCTC           100

TACGCGTAGT TAATTGGTTA GATGTCAACC CCCTCTCTAA GTGGCAGTAG           150

TGGGCTTGGT TATACCTGCT AGTGCCTGGG GATGTTCTAT TTTTCTAGTA           200

GTGCTTGATC AAACATTGCA TAGTTTGACT TGGGACAAAC TGTCTGATAT           250

ATATATATAT TTTTGGGCAG AGGGAGCAGT AAGAACTTAT TTAGAAATGT           300

AATCATTTGT TAAAAAGGT TTAATTTTGC TGCTTTCTTT CGTTAATGTT            350

GTTTTCACAT TAGATTTTCT TTGTGTTATA TACACTGGAT ACATACAAAT           400

TCAGTTGCAG TAGTCTCTTA ATCCACATCA GCTAGGCATA CTTTAGCAAA           450

AGCAAATTAC ACAAATCTAG TGTGCCTGTC GTCACATTCT CAATAAACTC           500

GTCATGTTTT ACTAAAAGTA CCTTTTCGAA GCATCATATT AATCCGAAAA           550

CAGTTAGGGA AGTCTCCAAA TCTGACCAAA TGCCAAGTCA TCGTCCAGCT           600

TATCAGCATC AACTTTCAG TTTCGCATGT GCTAGAAATT GTTTTTCATC            650

TACATGGCCA TTGTTGACTG CATGCATCTA TAAATAGGAC CTAGACGATC           700

AATCGCAATC GCATATCCAC TATTCTCTAG GAAGCAAGGG AATCACATCG           750

CC                                                              752
```

| | | | | | | | | | | | | | | |
|---|---|---|---|---|---|---|---|---|---|---|---|---|---|---|
| ATG | GCA | GCC | AAG | ATG | TTT | GCA | TTG | TTT | GCG | CTC | CTA | GCT | CTT | TGT | 797 |
| Met | Ala | Ala | Lys | Met | Phe | Ala | Leu | Phe | Ala | Leu | Leu | Ala | Leu | Cys | |
| | -20 | | | | -15 | | | | -10 | | | | | | |

```
GCA ACC GCC ACT AGT GCT ACC CAT ATC CCA GGG CAC TTG TCA CCA        842
Ala Thr Ala Thr Ser Ala Thr His Ile Pro Gly His Leu Ser Pro
    -5              1                5

CTA CTG ATG CCA TTG GCT ACC ATG AAC CCA TGG ATG CAG TAC TGC        887
Leu Leu Met Pro Leu Ala Thr Met Asn Pro Trp Met Gln Tyr Cys
10              15              20

ATG AAG CAA CAG GGG GTT GCC AAC TTG TTA GCG TGG CCG ACC CTG        932
Met Lys Gln Gln Gly Val Ala Asn Leu Leu Ala Trp Pro Thr Leu
25              30              35

ATG CTG CAG CAA CTG TTG GCC TCA CCG CTT CAG CAG TGC CAG ATG        977
Met Leu Gln Gln Leu Leu Ala Ser Pro Leu Gln Gln Cys Gln Met
40              45              50

CCA ATG ATG ATG CCG GGT ATG ATG CCA CCG ATG ACG ATG ATG CCG       1022
Pro Met Met Met Pro Gly Met Met Pro Pro Met Thr Met Met Pro
55              60              65

ATG CCG AGT ATG ATG CCA TCG ATG ATG GTG CCG ACT ATG ATG TCA       1067
Met Pro Ser Met Met Pro Ser Met Met Val Pro Thr Met Met Ser
70              75              80

CCA ATG ACG ATG GCT AGT ATG ATG CCG CCG ATG ATG ATG CCA AGC       1112
Pro Met Thr Met Ala Ser Met Met Pro Pro Met Met Met Pro Ser
85              90              95

ATG ATT TCA CCA ATG ACG ATG CCG AGT ATG ATG CCT TCG ATG ATA       1157
Met Ile Ser Pro Met Thr Met Pro Ser Met Met Pro Ser Met Ile
100             105             110

ATG CCG ACC ATG ATG TCA CCA ATG ATT ATG CCG AGT ATG ATG CCA       1202
Met Pro Thr Met Met Ser Pro Met Ile Met Pro Ser Met Met Pro
115             120             125

CCA ATG ATG ATG CCG AGC ATG GTG TCA CCA ATG ATG ATG CCA AAC       1247
Pro Met Met Met Pro Ser Met Val Ser Pro Met Met Met Pro Asn
130             135             140
```

-continued

```
ATG ATG ACA GTG CCA CAA TGT TAC TCT GGT TCT ATC TCA CAC ATT         1292
Met Met Thr Val Pro Gln Cys Tyr Ser Gly Ser Ile Ser His Ile
145                 150                 155

ATA CAA CAA CAA CAA TTA CCA TTC ATG TTC AGC CCC ACA GCC ATG         1337
Ile Gln Gln Gln Gln Leu Pro Phe Met Phe Ser Pro Thr Ala Met
160                 165                 170

GCG ATC CCA CCC ATG TTC TTA CAG CAG CCC TTT GTT GGT GCT GCA         1382
Ala Ile Pro Pro Met Phe Leu Gln Gln Pro Phe Val Gly Ala Ala
175                 180                 185

TTC TAG    ATCTAGATAT AA                                            1400
Phe
190

GCATTTGTGT AGTACCCAAT AATGAAGTCG GCATGCCATC GCATACGACT               1450

CATTGTTTAG GAATAAAACA AGCTAATAAT GACTTTTCTC TCATTATAAC               1500

TTATATCTCT CCATGTCTGT TTGTGTGTTT GTAATGTCTG TTAATCTTAG               1550

TAGATTATAT TGTATATATA ACCATGTATT CTCTCCATTC CAAATTATAG               1600

GTCTTGCATT TCAAGATAAA TAGTTTTAAC CATACCTAGA CATTATGTAT               1650

ATATAGGCGG CTTAACAAAA GCTATGTACT CAGTAAAATC AAAACGACTT               1700

ACAATTTAAA ATTTAGAAAG TACATTTTTA TTAATAGACT AGGTGAGTAC               1750

TTGTGCGTTG CAACGGGAAC ATATAATAAC ATAATAACTT ATATACAAAA               1800

TGTATCTTAT ATTGTTATAA AAAATATTTC ATAATCCATT TGTAATCCTA               1850

GTCATACATA AATTTTGTTA TTTTAATTTA GTTGTTTCAC TACTACATTG               1900

CAACCATTAG TATCATGCAG ACTTCGATAT ATGCCAAGAT TTGCATGGTC               1950

TCATCATTGA AGAGCACATG TCACACCTGC CGGTAGAAGT TCTCTCGTAC               2000

ATTGTCAGTC ATCAGGTACG CACCACCATA CACGCTTGCT TAAACAAAAA               2050

AACAAGTGTA TGTGTTTGCG AAGAGAATTA AGACAGGCAG ACACAAAGCT               2100

ACCCGACGAT GGCGAGTCGG TCA                                           2123

(2) INFORMATION FOR SEQ ID NO:2:

(i) SEQUENCE CHARACTERISTICS:
        (A) LENGTH:   639 nucleotides (B) TYPE: Nucleic Acid (C) STRANDEDNESS: single (D) TOPOLOGY:  linear (ii) MOLECULE TYPE:  in vitro mutated genomic DNA (x) PUBLICATION INFORMATION:  unpublished sequence (xi) SEQUENCE DESCRIPTION:  SEQ ID NO:2:

CC ATG GCA GCC AAG ATG TTT GCA TTG TTT GCG CTC CTA GCT CTT TGT       47
   Met Ala Ala Lys Met Phe Ala Leu Phe Ala Leu Leu Ala Leu Cys
       -20                 -15                 -10

GCA ACC GCC ACT AGT GCT ACC CAT ATC CCA GGG CAC TTG TCA CCA          92
Ala Thr Ala Thr Ser Ala Thr His Ile Pro Gly His Leu Ser Pro
     -5                  1                   5

CTA CTG ATG CCA TTG GCT ACC ATG AAC CCT TGG ATG CAG TAC TGC         137
Leu Leu Met Pro Leu Ala Thr Met Asn Pro Trp Met Gln Tyr Cys
10                  15                  20

ATG AAG CAA CAG GGG GTT GCC AAC TTG TTA GCG TGG CCG ACC CTG         182
Met Lys Gln Gln Gly Val Ala Asn Leu Leu Ala Trp Pro Thr Leu
25                  30                  35
```

| | |
|---|---|
| ATG CTG CAG CAA CTG TTG GCC TCA CCG CTT CAG CAG TGC CAG ATG<br>Met Leu Gln Gln Leu Leu Ala Ser Pro Leu Gln Gln Cys Gln Met<br>40                        45                       50 | 227 |
| CCA ATG ATG ATG CCG GGT ATG ATG CCA CCG ATG ACG ATG ATG CCG<br>Pro Met Met Met Pro Gly Met Met Pro Pro Met Thr Met Met Pro<br>55                        60                       65 | 272 |
| ATG CCG AGT ATG ATG CCA TCG ATG ATG GTG CCG ACT ATG ATG TCA<br>Met Pro Ser Met Met Pro Ser Met Met Val Pro Thr Met Met Ser<br>70                        75                       80 | 317 |
| CCA ATG ACG ATG GCT AGT ATG ATG CCG CCG ATG ATG ATG CCA AGC<br>Pro Met Thr Met Ala Ser Met Met Pro Pro Met Met Met Pro Ser<br>85                        90                       95 | 362 |
| ATG ATT TCA CCA ATG ACG ATG CCG AGT ATG ATG CCT TCG ATG ATA<br>Met Ile Ser Pro Met Thr Met Pro Ser Met Met Pro Ser Met Ile<br>100                      105                   110 | 407 |
| ATG CCG ACC ATG ATG TCA CCA ATG ATT ATG CCG AGT ATG ATG CCA<br>Met Pro Thr Met Met Ser Pro Met Ile Met Pro Ser Met Met Pro<br>115                      120                   125 | 452 |
| CCA ATG ATG ATG CCG AGC ATG GTG TCA CCA ATG ATG ATG CCA AAC<br>Pro Met Met Met Pro Ser Met Val Ser Pro Met Met Met Pro Asn<br>130                      135                   140 | 497 |
| ATG ATG ACA GTG CCA CAA TGT TAC TCT GGT TCT ATC TCA CAC ATT<br>Met Met Thr Val Pro Gln Cys Tyr Ser Gly Ser Ile Ser His Ile<br>145                      150                   155 | 542 |
| ATA CAA CAA CAA CAA TTA CCA TTC ATG TTC AGC CCC ACA GCA ATG<br>Ile Gln Gln Gln Gln Leu Pro Phe Met Phe Ser Pro Thr Ala Met<br>160                      165                   170 | 587 |
| GCG ATC CCA CCC ATG TTC TTA CAG CAG CCC TTT GTT GGT GCT GCA<br>Ala Ile Pro Pro Met Phe Leu Gln Gln Pro Phe Val Gly Ala Ala<br>175                      180                   185 | 632 |
| TTC TAG A<br>Phe<br>190 | 639 |

(2) INFORMATION FOR SEQ ID NO:3:

(i) SEQUENCE CHARACTERISTICS:
        (A) LENGTH:  579 nucleotides (B) TYPE: Nucleic Acid (C) STRANDEDNESS:  single (D) TOPOLOGY:  linear (ii) MOLECULE TYPE:  in vitro mutated genomic DNA (x) PUBLICATION INFORMATION:  unpublished sequence (xi) SEQUENCE DESCRIPTION: SEQ ID NO:3:

| | |
|---|---|
| TC ATG ACC CAT ATC CCA GGG CAC TTG TCA CCA CTA CTG ATG CCA TTG<br>   Met Thr His Ile Pro Gly His Leu Ser Pro Leu Leu Met Pro Leu<br>                  5                      10                      15 | 47 |
| GCT ACC ATG AAC CCT TGG ATG CAG TAC TGC ATG AAG CAA CAG GGG<br>Ala Thr Met Asn Pro Trp Met Gln Tyr Cys Met Lys Gln Gln Gly<br>           20                     25                     30 | 92 |
| GTT GCC AAC TTG TTA GCG TGG CCG ACC CTG ATG CTG CAG CAA CTG<br>Val Ala Asn Leu Leu Ala Trp Pro Thr Leu Met Leu Gln Gln Leu<br>           35                     40                     45 | 137 |
| TTG GCC TCA CCG CTT CAG CAG TGC CAG ATG CCA ATG ATG ATG CCG<br>Leu Ala Ser Pro Leu Gln Gln Cys Gln Met Pro Met Met Met Pro<br>           50                     55                     60 | 182 |

-continued

```
GGT ATG ATG CCA CCG ATG ACG ATG ATG CCG ATG CCG AGT ATG ATG        227
Gly Met Met Pro Pro Met Thr Met Met Pro Met Pro Ser Met Met
             65                  70                  75

CCA TCG ATG ATG GTG CCG ACT ATG ATG TCA CCA ATG ACG ATG GCT        272
Pro Ser Met Met Val Pro Thr Met Met Ser Pro Met Thr Met Ala
             80                  85                  90

AGT ATG ATG CCG CCG ATG ATG ATG CCA AGC ATG ATT TCA CCA ATG        317
Ser Met Met Pro Pro Met Met Met Pro Ser Met Ile Ser Pro Met
             95                 100                 105

ACG ATG CCG AGT ATG ATG CCT TCG ATG ATA ATG CCG ACC ATG ATG        362
Thr Met Pro Ser Met Met Pro Ser Met Ile Met Pro Thr Met Met
            110                 115                 120

TCA CCA ATG ATT ATG CCG AGT ATG ATG CCA CCA ATG ATG ATG CCG        407
Ser Pro Met Ile Met Pro Ser Met Met Pro Pro Met Met Met Pro
            125                 130                 135

AGC ATG GTG TCA CCA ATG ATG ATG CCA AAC ATG ATG ACA GTG CCA        452
Ser Met Val Ser Pro Met Met Met Pro Asn Met Met Thr Val Pro
            140                 145                 150

CAA TGT TAC TCT GGT TCT ATC TCA CAC ATT ATA CAA CAA CAA CAA        497
Gln Cys Tyr Ser Gly Ser Ile Ser His Ile Ile Gln Gln Gln Gln
            155                 160                 165

TTA CCA TTC ATG TTC AGC CCC ACA GCA ATG GCG ATC CCA CCC ATG        542
Leu Pro Phe Met Phe Ser Pro Thr Ala Met Ala Ile Pro Pro Met
            170                 175                 180

TTC TTA CAG CAG CCC TTT GTT GGT GCT GCA TTC TAG A                  579
Phe Leu Gln Gln Pro Phe Val Gly Ala Ala Phe
            185                 190
```

(2) INFORMATION FOR SEQ ID NO:4:

(i) SEQUENCE CHARACTERISTICS:
        (A) LENGTH: 281 nucleotides (B) TYPE: Nucleic Acid (C) STRANDEDNESS: single (D) TOPOLOGY: linear (ii) MOLECULE TYPE: in vitro mutated genomic DNA (x) PUBLICATION INFORMATION: unpublished sequence (xi) SEQUENCE DESCRIPTION: SEQ ID NO:4:

```
CAT ATG CCA ATG ATG ATG CCG GGT ATG ATG CCA CCG ATG ACG ATG         45
    Met Pro Met Met Met Pro Gly Met Met Pro Pro Met Thr Met
                     5                  10

ATG CCG ATG CCG AGT ATG ATG CCA TCG ATG ATG GTG CCG ACT ATG         90
Met Pro Met Pro Ser Met Met Pro Ser Met Met Val Pro Thr Met
 15                  20                  25

ATG TCA CCA ATG ACG ATG GCT AGT ATG ATG CCG CCG ATG ATG ATG        135
Met Ser Pro Met Thr Met Ala Ser Met Met Pro Pro Met Met Met
 30                  35                  40

CCA AGC ATG ATT TCA CCA ATG ACG ATG CCG AGT ATG ATG CCT TCG        180
Pro Ser Met Ile Ser Pro Met Thr Met Pro Ser Met Met Pro Ser
 45                  50                  55

ATG ATA ATG CCG ACC ATG ATG TCA CCA ATG ATT ATG CCG AGT ATG        225
Met Ile Met Pro Thr Met Met Ser Pro Met Ile Met Pro Ser Met
 60                  65                  70

ATG CCA CCA ATG ATG ATG CCG AGC ATG GTG TCA CCA ATG ATG ATG        270
Met Pro Pro Met Met Met Pro Ser Met Val Ser Pro Met Met Met
 75                  80                  85

CCA TAG AATTC                                                      281
```

Pro
90

(2) INFORMATION FOR SEQ ID NO:5:

(i) SEQUENCE CHARACTERISTICS:
        (A) LENGTH: 453 nucleotides (B) TYPE: Nucleic Acid (C) STRANDEDNESS: single (D) TOPOLOGY: linear (ii) MOLECULE TYPE: cDNA (x) PUBLICATION INFORMATION:
        (A) AUTHORS: Kirihara,J.A.

Hunsperger,J.P.
           Mahoney,W.C.
           Messing,J.W.
        (B) TITLE: Differential expression of a gene for a methionine-
           rich storage protein in
           maize
        (C) JOURNAL: Mol. Gen. Genet.

(D) VOLUME: 211

(F) PAGES: 477-484

(G) DATE: 1988

(K) RELEVANT RESIDUES IN SEQ ID NO:

NO:5: from 22 to 474

(xi) SEQUENCE DESCRIPTION: SEQ ID NO:5:

```
ATG GCA GCC AAG ATG CTT GCA TTG TTC GCT CTC CTA GCT CTT TGT        45
Met Ala Ala Lys Met Leu Ala Leu Phe Ala Leu Leu Ala Leu Cys
    -20             -15                 -10

GCA AGC GCC ACT AGT GCG ACC CAT ATT CCA GGG CAC TTG CCA CCA        90
Ala Ser Ala Thr Ser Ala Thr His Ile Pro Gly His Leu Pro Pro
    -5              1                   5

GTC ATG CCA TTG GGT ACC ATG AAC CCA TGC ATG CAG TAC TGC ATG       135
Val Met Pro Leu Gly Thr Met Asn Pro Cys Met Gln Tyr Cys Met
10              15                  20

ATG CAA CAG GGG CTT GCC AGC TTG ATG GCG TGT CCG TCC CTG ATG       180
Met Gln Gln Gly Leu Ala Ser Leu Met Ala Cys Pro Ser Leu Met
25              30                  35

CTG CAG CAA CTG TTG GCC TTA CCG CTT CAG ACG ATG CCA GTG ATG       225
Leu Gln Gln Leu Leu Ala Leu Pro Leu Gln Thr Met Pro Val Met
40              45                  50

ATG CCA CAG ATG ATG ACG CCT AAC ATG ATG TCA CCA TTG ATG ATG       270
Met Pro Gln Met Met Thr Pro Asn Met Met Ser Pro Leu Met Met
55              60                  65

CCG AGC ATG ATG TCA CCA ATG GTC TTG CCG AGC ATG ATG TCG CAA       315
Pro Ser Met Met Ser Pro Met Val Leu Pro Ser Met Met Ser Gln
70              75                  80

ATG ATG ATG CCA CAA TGT CAC TGC GAC GCC GTC TCG CAG ATT ATG       360
Met Met Met Pro Gln Cys His Cys Asp Ala Val Ser Gln Ile Met
85              90                  95

CTG CAA CAG CAG TTA CCA TTC ATG TTC AAC CCA ATG GCC ATG ACG       405
Leu Gln Gln Gln Leu Pro Phe Met Phe Asn Pro Met Ala Met Thr
100             105                 110

ATT CCA CCC ATG TTC TTA CAG CAA CCC TTT GTT GGT GCT GCA TTC       450
```

```
Ile Pro Pro Met Phe Leu Gln Gln Pro Phe Val Gly Ala Ala Phe
115                 120                 125
TAG                                                                              453
```

(2) INFORMATION FOR SEQ ID NO:6:

(i) SEQUENCE CHARACTERISTICS:
        (A) LENGTH:  30 nucleotides (B) TYPE: Nucleic Acid (C) STRANDEDNESS:  single (D) TOPOLOGY:  linear (ii) MOLECULE TYPE:  in vitro synthesized DNA (x) PUBLICATION INFORMATION:  unpublished sequence (xi) SEQUENCE DESCRIPTION:  SEQ ID NO:6:

```
ATGGCAGCCA AGATGCTTGC ATTGTTCGCT                                                  30
```

(2) INFORMATION FOR SEQ ID NO:7:

(i) SEQUENCE CHARACTERISTICS:
        (A) LENGTH:  30 nucleotides (B) TYPE: Nucleic Acid (C) STRANDEDNESS:  single (D) TOPOLOGY:  linear (ii) MOLECULE TYPE:  in vitro synthesized DNA (x) PUBLICATION INFORMATION:  unpublished sequence (xi) SEQUENCE DESCRIPTION:  SEQ ID NO:7:

```
GAATGCAGCA CCAACAAAGG GTTGCTGTAA                                                  30
```

(2) INFORMATION FOR SEQ ID NO:8:

(i) SEQUENCE CHARACTERISTICS:
        (A) LENGTH:  17 nucleotides (B) TYPE: Nucleic Acid (C) STRANDEDNESS:  single (D) TOPOLOGY:  linear (ii) MOLECULE TYPE:  in vitro synthesized DNA (x) PUBLICATION INFORMATION:  unpublished sequence (xi) SEQUENCE DESCRIPTION:  SEQ ID NO:8:

```
ATGAACCCTT GGATGCA                                                                17
```

(2) INFORMATION FOR SEQ ID NO:9:

(i) SEQUENCE CHARACTERISTICS:
        (A) LENGTH:  17 nucleotides (B) TYPE: Nucleic Acid (C) STRANDEDNESS:  single (D) TOPOLOGY:  linear (ii) MOLECULE TYPE: in vitro synthesized DNA (x) PUBLICATION INFORMATION: unpublished sequence (xi) SEQUENCE DESCRIPTION: SEQ ID NO:9:

CCCACAGCAA TGGCGAT                                                          17

(2) INFORMATION FOR SEQ ID NO:10:

(i) SEQUENCE CHARACTERISTICS:
             (A) LENGTH: 13 nucleotides (B) TYPE: Nucleic Acid (C) STRANDEDNESS: single (D) TOPOLOGY: linear (ii) MOLECULE TYPE: in vitro synthesized DNA (x) PUBLICATION INFORMATION: unpublished sequence (xi) SEQUENCE DESCRIPTION: SEQ ID NO:10:

CTAGCCCGGG TAC                                                              13

(2) INFORMATION FOR SEQ ID NO:11:

(i) SEQUENCE CHARACTERISTICS:
             (A) LENGTH: 13 nucleotides (B) TYPE: Nucleic Acid (C) STRANDEDNESS: single (D) TOPOLOGY: linear (ii) MOLECULE TYPE: in vitro synthesized DNA (x) PUBLICATION INFORMATION: unpublished
                sequence (xi) SEQUENCE DESCRIPTION: SEQ ID NO:11:

CTAGGTACCC GGG                                                              13

(2) INFORMATION FOR SEQ ID NO:12:

(i) SEQUENCE CHARACTERISTICS:
             (A) LENGTH: 30 nucleotides (B) TYPE: Nucleic Acid (C) STRANDEDNESS: single (D) TOPOLOGY: linear (ii) MOLECULE TYPE: in vitro synthesized DNA (x) PUBLICATION INFORMATION: unpublished sequence (xi) SEQUENCE DESCRIPTION: SEQ ID NO:12:

CCACTTCATG ACCCATATCC CAGGGCACTT                                            30

(2) INFORMATION FOR SEQ ID NO:13:

(i) SEQUENCE CHARACTERISTICS:
             (A) LENGTH: 30 nucleotides (B) TYPE: Nucleic Acid (C) STRANDEDNESS: single (D) TOPOLOGY: linear (ii) MOLECULE TYPE: in vitro synthesized DNA (x) PUBLICATION INFORMATION: unpublished
    sequence (xi) SEQUENCE DESCRIPTION: SEQ ID NO:13:

TTCTATCTAG AATGCAGCAC CAACAAAGGG                                30

(2) INFORMATION FOR SEQ ID NO:14:

(i) SEQUENCE CHARACTERISTICS:
    (A) LENGTH: 30 nucleotides (B) TYPE: Nucleic Acid (C) STRANDEDNESS: single (D) TOPOLOGY: linear (ii) MOLECULE TYPE: in vitro synthesized DNA (x) PUBLICATION INFORMATION: unpublished sequence (xi) SEQUENCE DESCRIPTION: SEQ ID NO:14:

TCACCGCTTC AGCAGTGCCA TATGCCAATG                                30

(2) INFORMATION FOR SEQ ID NO:15:

(i) SEQUENCE CHARACTERISTICS:
    (A) LENGTH: 40 nucleotides (B) TYPE: Nucleic Acid (C) STRANDEDNESS: single (D) TOPOLOGY: linear (ii) MOLECULE TYPE: in vitro synthesized DNA (x) PUBLICATION INFORMATION: unpublished sequence (xi) SEQUENCE DESCRIPTION: SEQ ID NO:15:

TCTTAGAATT CTATGGCATC ATCATTGGTG ACACCATGCT                     40

(2) INFORMATION FOR SEQ ID NO:16:

(i) SEQUENCE CHARACTERISTICS:
    (A) LENGTH: 71 base pairs (B) TYPE: nucleic acid (C) STRANDEDNESS: single (D) TOPOLOGY: linear (ii) MOLECULE TYPE: in vitro synthesized DNA (ix) FEATURE:
    (A) NAME/KEY: CDS (B) LOCATION: 2..70

(xi) SEQUENCE DESCRIPTION: SEQ ID NO:16:

```
C ATG ATG AGA GCA AGG GTT CCA CTC CTG TTG CTG GGA ATT CTT TTC        46
  Met Met Arg Ala Arg Val Pro Leu Leu Leu Leu Gly Ile Leu Phe
  1               5                   10                  15

CTG GCA TCA CTT TCT GCT AGC TTT G                                    71
Leu Ala Ser Leu Ser Ala Ser Phe
            20
```

(2) INFORMATION FOR SEQ ID NO:17:

(i) SEQUENCE CHARACTERISTICS:
        (A) LENGTH:  71 base pairs (B) TYPE:  nucleic acid (C) STRANDEDNESS:  single (D) TOPOLOGY:  linear (ii) MOLECULE TYPE:  in vitro synthesized DNA (xi) SEQUENCE DESCRIPTION:  SEQ ID NO:17:

```
CTAGCAAAGC TAGCAGAAAG TGATGCCAGG AAAAGAATTC CCAGCAACAG GAGTGGAACC    60

CTTGCTCTCA T                                                         71
```

(2) INFORMATION FOR SEQ ID NO:18:

(i) SEQUENCE CHARACTERISTICS:
        (A) LENGTH:  653 base pairs (B) TYPE:  nucleic acid (C) STRANDEDNESS:  single (D) TOPOLOGY:  linear (ii) MOLECULE TYPE: Nucleic Acid (genomic)

(vii) IMMEDIATE SOURCE:
        (B) CLONE:  pCC18

(ix) FEATURE:
        (A) NAME/KEY:  CDS (B) LOCATION:  2..652

(xi) SEQUENCE DESCRIPTION:  SEQ ID NO:18:

```
C ATG ATG AGA GCA AGG GTT CCA CTC CTG TTG CTG GGA ATT CTT TTC        46
  Met Met Arg Ala Arg Val Pro Leu Leu Leu Leu Gly Ile Leu Phe
  1               5                   10                  15

CTG GCA TCA CTT TCT GCT AGC TTT GCT AGT GCT ACC CAT ATC CCA GGG      94
Leu Ala Ser Leu Ser Ala Ser Phe Ala Ser Ala Thr His Ile Pro Gly
            20                  25                  30

CAC TTG TCA CCA CTA CTG ATG CCA TTG GCT ACC ATG AAC CCT TGG ATG     142
His Leu Ser Pro Leu Leu Met Pro Leu Ala Thr Met Asn Pro Trp Met
        35                  40                  45

CAG TAC TGC ATG AAG CAA CAG GGG GTT GCC AAC TTG TTA GCG TGG CCG     190
Gln Tyr Cys Met Lys Gln Gln Gly Val Ala Asn Leu Leu Ala Trp Pro
    50                  55                  60

ACC CTG ATG CTG CAG CAA CTG TTG GCC TCA CCG CTT CAG CAG TGC CAG     238
Thr Leu Met Leu Gln Gln Leu Leu Ala Ser Pro Leu Gln Gln Cys Gln
65                  70                  75

ATG CCA ATG ATG ATG CCG GGT ATG ATG CCA CCG ATG ACG ATG ATG CCG     286
Met Pro Met Met Met Pro Gly Met Met Pro Pro Met Thr Met Met Pro
80                  85                  90                  95
```

```
ATG CCG AGT ATG ATG CCA TCG ATG ATG GTG CCG ACT ATG ATG TCA CCA         334
Met Pro Ser Met Met Pro Ser Met Met Val Pro Thr Met Met Ser Pro
            100                 105                 110

ATG ACG ATG GCT AGT ATG ATG CCG CCG ATG ATG ATG CCA AGC ATG ATT         382
Met Thr Met Ala Ser Met Met Pro Pro Met Met Met Pro Ser Met Ile
            115                 120                 125

TCA CCA ATG ACG ATG CCG AGT ATG ATG CCT TCG ATG ATA ATG CCG ACC         430
Ser Pro Met Thr Met Pro Ser Met Met Pro Ser Met Ile Met Pro Thr
        130                 135                 140

ATG ATG TCA CCA ATG ATT ATG CCG AGT ATG ATG CCA CCA ATG ATG ATG         478
Met Met Ser Pro Met Ile Met Pro Ser Met Met Pro Pro Met Met Met
        145                 150                 155

CCG AGC ATG GTG TCA CCA ATG ATG ATG CCA AAC ATG ATG ACA GTG CCA         526
Pro Ser Met Val Ser Pro Met Met Met Pro Asn Met Met Thr Val Pro
160                 165                 170                 175

CAA TGT TAC TCT GGT TCT ATC TCA CAC ATT ATA CAA CAA CAA CAA TTA         574
Gln Cys Tyr Ser Gly Ser Ile Ser His Ile Ile Gln Gln Gln Gln Leu
                180                 185                 190

CCA TTC ATG TTC AGC CCC ACA GCA ATG GCG ATC CCA CCC ATG TTC TTA         622
Pro Phe Met Phe Ser Pro Thr Ala Met Ala Ile Pro Pro Met Phe Leu
            195                 200                 205

CAG CAG CCC TTT GTT GGT GCT GCA TTC TAGA                                653
Gln Gln Pro Phe Val Gly Ala Ala Phe
        210                 215

(2) INFORMATION FOR SEQ ID NO:19:

(i) SEQUENCE CHARACTERISTICS:
        (A) LENGTH:  31 base pairs (B) TYPE:  nucleic acid (C) STRANDEDNESS:  single (D) TOPOLOGY:  linear (ii) MOLECULE TYPE:  in vitro synthesized DNA (xi) SEQUENCE DESCRIPTION:  SEQ ID NO:19:

TTCTGCTAGC TTTGCTACCC ATATCCCAGG G                                       31

(2) INFORMATION FOR SEQ ID NO:20:

(i) SEQUENCE CHARACTERISTICS:
        (A) LENGTH:  647 base pairs (B) TYPE:  nucleic acid (C) STRANDEDNESS:  single (D) TOPOLOGY:  linear (ii) MOLECULE TYPE: Nucleic Acid (genomic)

(ix) FEATURE:
        (A) NAME/KEY:  CDS (B) LOCATION:  2..646

(xi) SEQUENCE DESCRIPTION:  SEQ ID NO:20:

C ATG ATG AGA GCA AGG GTT CCA CTC CTG TTG CTG GGA ATT CTT TTC           46
  Met Met Arg Ala Arg Val Pro Leu Leu Leu Leu Gly Ile Leu Phe
  1               5                  10                  15

CTG GCA TCA CTT TCT GCT AGC TTT GCT ACC CAT ATC CCA GGG CAC TTG         94
Leu Ala Ser Leu Ser Ala Ser Phe Ala Thr His Ile Pro Gly His Leu
```

```
                        20                      25                      30
TCA CCA CTA CTG ATG CCA TTG GCT ACC ATG AAC CCT TGG ATG CAG TAC         142
Ser Pro Leu Leu Met Pro Leu Ala Thr Met Asn Pro Trp Met Gln Tyr
            35                      40                      45

TGC ATG AAG CAA CAG GGG GTT GCC AAC TTG TTA GCG TGG CCG ACC CTG         190
Cys Met Lys Gln Gln Gly Val Ala Asn Leu Leu Ala Trp Pro Thr Leu
        50                      55                      60

ATG CTG CAG CAA CTG TTG GCC TCA CCG CTT CAG CAG TGC CAG ATG CCA         238
Met Leu Gln Gln Leu Leu Ala Ser Pro Leu Gln Gln Cys Gln Met Pro
    65                      70                      75

ATG ATG ATG CCG GGT ATG ATG CCA CCG ATG ACG ATG ATG CCG ATG CCG         286
Met Met Met Pro Gly Met Met Pro Pro Met Thr Met Met Pro Met Pro
80                      85                      90                  95

AGT ATG ATG CCA TCG ATG ATG GTG CCG ACT ATG ATG TCA CCA ATG ACG         334
Ser Met Met Pro Ser Met Met Val Pro Thr Met Met Ser Pro Met Thr
                100                     105                     110

ATG GCT AGT ATG ATG CCG CCG ATG ATG ATG CCA AGC ATG ATT TCA CCA         382
Met Ala Ser Met Met Pro Pro Met Met Met Pro Ser Met Ile Ser Pro
            115                     120                     125

ATG ACG ATG CCG AGT ATG ATG CCT TCG ATG ATA ATG CCG ACC ATG ATG         430
Met Thr Met Pro Ser Met Met Pro Ser Met Ile Met Pro Thr Met Met
        130                     135                     140

TCA CCA ATG ATT ATG CCG AGT ATG ATG CCA CCA ATG ATG ATG CCG AGC         478
Ser Pro Met Ile Met Pro Ser Met Met Pro Pro Met Met Met Pro Ser
    145                     150                     155

ATG GTG TCA CCA ATG ATG ATG CCA AAC ATG ATG ACA GTG CCA CAA TGT         526
Met Val Ser Pro Met Met Met Pro Asn Met Met Thr Val Pro Gln Cys
160                     165                     170                 175

TAC TCT GGT TCT ATC TCA CAC ATT ATA CAA CAA CAA CAA TTA CCA TTC         574
Tyr Ser Gly Ser Ile Ser His Ile Ile Gln Gln Gln Gln Leu Pro Phe
                180                     185                     190

ATG TTC AGC CCC ACA GCA ATG GCG ATC CCA CCC ATG TTC TTA CAG CAG         622
Met Phe Ser Pro Thr Ala Met Ala Ile Pro Pro Met Phe Leu Gln Gln
            195                     200                     205

CCC TTT GTT GGT GCT GCA TTC TAGA                                        647
Pro Phe Val Gly Ala Ala Phe
        210                     215
```

(2) INFORMATION FOR SEQ ID NO:21:

(i) SEQUENCE CHARACTERISTICS:
        (A) LENGTH: 30 base pairs (B) TYPE: nucleic acid (C) STRANDEDNESS: single (D) TOPOLOGY: linear (ii) MOLECULE TYPE: in vitro synthesized DNA (xi) SEQUENCE DESCRIPTION: SEQ ID NO:21:

```
ACTAATCATG ATGAGAGCAA GGGTTCCACT                                         30
```

(2) INFORMATION FOR SEQ ID NO:22:

(i) SEQUENCE CHARACTERISTICS:
        (A) LENGTH: 30 base pairs (B) TYPE: nucleic acid (C) STRANDEDNESS: single (D) TOPOLOGY: linear

```
        (ii) MOLECULE TYPE:  in vitro synthesized DNA (xi) SEQUENCE DESCRIPTION: SEQ ID NO:22:

GAATGCAGCA CCAACAAAGG GTTGCTGTAA                                              30

(2) INFORMATION FOR SEQ ID NO:23:

(i) SEQUENCE CHARACTERISTICS:
            (A) LENGTH:  38 base pairs (B) TYPE:  nucleic acid (C) STRANDEDNESS:  single (D) TOPOLOGY:  linear (ii) MOLECULE TYPE:  in vitro synthesized DNA (ix) FEATURE:
            (A) NAME/KEY:  CDS (B) LOCATION:  6..38

(xi) SEQUENCE DESCRIPTION: SEQ ID NO:23:

TGCTTT GCT AGC TTT GCT ATG CCA ATG ATG ATG CCG GGT                            38
       Ala Ser Phe Ala Met Pro Met Met Met Pro Gly
       1            5                          10

(2) INFORMATION FOR SEQ ID NO:24:

(i) SEQUENCE CHARACTERISTICS:
            (A) LENGTH:  36 base pairs (B) TYPE:  nucleic acid (C) STRANDEDNESS:  single (D) TOPOLOGY:  linear (ii) MOLECULE TYPE:  in vitro synthesized DNA (xi) SEQUENCE DESCRIPTION: SEQ ID NO:24:

TGCTTTCTAG ACTATGGCAT CATCATTGGT GACACC                                       36

(2) INFORMATION FOR SEQ ID NO:25:

(i) SEQUENCE CHARACTERISTICS:
            (A) LENGTH:  352 base pairs (B) TYPE:  nucleic acid (C) STRANDEDNESS:  single (D) TOPOLOGY:  linear (ii) MOLECULE TYPE: Nucleic Acid (genomic)

(ix) FEATURE:
            (A) NAME/KEY:  CDS (B) LOCATION:  2..346

(xi) SEQUENCE DESCRIPTION: SEQ ID NO:25:

C ATG ATG AGA GCA AGG GTT CCA CTC CTG TTG CTG GGA ATT CTT TTC                 46
  Met Met Arg Ala Arg Val Pro Leu Leu Leu Leu Gly Ile Leu Phe
  1           5                  10                  15
```

```
CTG GCA TCA CTT TCT GCT AGC TTT GCT ATG CCA ATG ATG ATG CCG GGT         94
Leu Ala Ser Leu Ser Ala Ser Phe Ala Met Pro Met Met Met Pro Gly
                20                  25                  30

ATG ATG CCA CCG ATG ACG ATG ATG CCG ATG CCG AGT ATG ATG CCA TCG        142
Met Met Pro Pro Met Thr Met Met Pro Met Pro Ser Met Met Pro Ser
            35                  40                  45

ATG ATG GTG CCG ACT ATG ATG TCA CCA ATG ACG ATG GCT AGT ATG ATG        190
Met Met Val Pro Thr Met Met Ser Pro Met Thr Met Ala Ser Met Met
        50                  55                  60

CCG CCG ATG ATG ATG CCA AGC ATG ATT TCA CCA ATG ACG ATG CCG AGT        238
Pro Pro Met Met Met Pro Ser Met Ile Ser Pro Met Thr Met Pro Ser
        65                  70                  75

ATG ATG CCT TCG ATG ATA ATG CCG ACC ATG ATG TCA CCA ATG ATT ATG        286
Met Met Pro Ser Met Ile Met Pro Thr Met Met Ser Pro Met Ile Met
80                  85                  90                  95

CCG AGT ATG ATG CCA CCA ATG ATG ATG CCG AGC ATG GTG TCA CCA ATG        334
Pro Ser Met Met Pro Pro Met Met Met Pro Ser Met Val Ser Pro Met
                100                 105                 110

ATG ATG CCA TAGTCTAGA                                                   352
Met Met Pro
        115

(2) INFORMATION FOR SEQ ID NO:26:

(i) SEQUENCE CHARACTERISTICS:
        (A) LENGTH: 3237 base pairs (B) TYPE: nucleic acid (C) STRANDEDNESS: single (D) TOPOLOGY: linear (ii) MOLECULE TYPE: Nucleic Acid (genomic)

(ix) FEATURE:
        (A) NAME/KEY: CDS (B) LOCATION: 1419..2444

(xi) SEQUENCE DESCRIPTION: SEQ ID NO:26:

GTCGACTCTA GAGGATCCAA TTCCAATCCC ACAAAAATCT GAGCTTAACA GCACAGTTGC        60

TCCTCTCAGA GCAGAATCGG GTATTCAACA CCCTCATATC AACTACTACG TTGTGTATAA       120

CGGTCCACAT GCCGGTATAT ACGATGACTG GGGTTGTACA AAGGCGGCAA CAAACGGCGT       180

TCCCGGAGTT GCACACAAGA AATTTGCCAC TATTACAGAG GCAAGAGCAG CAGCTGACGC       240

GTACACAACA AGTCAGCAAA CAGACAGGTT GAACTTCATC CCCAAAGGAG AAGCTCAACT       300

CAAGCCCAAG AGCTTTGCTA AGGCCCTAAC AAGCCCACCA AAGCAAAAAG CCCACTGGCT       360

CACGCTAGGA ACCAAAAGGC CCAGCAGTGA TCCAGCCCCA AAAGAGATCT CCTTTGCCCC       420

GGAGATTACA ATGGACGATT TCCTCTATCT TTACGATCTA GGAAGGAAGT TCGAAGGTGA       480

AGGTGACGAC ACTATGTTCA CCACTGATAA TGAGAAGGTT AGCCTCTTCA ATTTCAGAAA       540

GAATGCTGAC CCACAGATGG TTAGAGAGGC CTACGCAGCA GGTCTCATCA AGACGATCTA       600

CCCGAGTAAC AATCTCCAGG AGATCAAATA CCTTCCCAAG AAGGTTAAAG ATGCAGTCAA       660

AAGATTCAGG ACTAATTGCA TCAAGAACAC AGAGAAAGAC ATATTTCTCA AGATCAGAAG       720

TACTATTCCA GTATGGACGA TTCAAGGCTT GCTTCATAAA CCAAGGCAAG TAATAGAGAT       780

TGGAGTCTCT AAAAAGGTAG TTCCTACTGA ATCTAAGGCC ATGCATGGAG TCTAAGATTC       840
```

```
AAATCGAGGA TCTAACAGAA CTCGCCGTGA AGACTGGCGA ACAGTTCATA CAGAGTCTTT      900

TACGACTCAA TGACAAGAAG AAAATCTTCG TCAACATGGT GGAGCACGAC ACTCTGGTCT      960

ACTCCAAAAA TGTCAAAGAT ACAGTCTCAG AAGACCAAAG GGCTATTGAG ACTTTTCAAC     1020

AAAGGATAAT TTCGGGAAAC CTCCTCGGAT TCCATTGCCC AGCTATCTGT CACTTCATCG     1080

AAAGGACAGT AGAAAGGAA GGTGGCTCCT ACAAATGCCA TCATTGCGAT AAAGGAAAGG     1140

CTATCATTCA AGATGCCTCT GCCGACAGTG GTCCCAAAGA TGGACCCCCA CCCACGAGGA     1200

GCATCGTGGA AAAGAAGAC GTTCCAACCA CGTCTTCAAA GCAAGTGGAT TGATGTGACA     1260

TCTCCACTGA CGTAAGGGAT GACGCACAAT CCCACTATCC TTCGCAAGAC CCTTCCTCTA     1320

TATAAGGAAG TTCATTTCAT TTGGAGAGGA CACGCTCGAG CTCATTTCTC TATTACTTCA     1380

GCCATAACAA AAGAACTCTT TTCTCTTCTT ATTAAACC ATG AAA AAG CCT GAA        1433
                                          Met Lys Lys Pro Glu
                                            1               5

CTC ACC GCG ACG TCT GTC GAG AAG TTT CTG ATC GAA AAG TTC GAC AGC      1481
Leu Thr Ala Thr Ser Val Glu Lys Phe Leu Ile Glu Lys Phe Asp Ser
             10                  15                  20

GTC TCC GAC CTG ATG CAG CTC TCG GAG GGC GAA GAA TCT CGT GCT TTC      1529
Val Ser Asp Leu Met Gln Leu Ser Glu Gly Glu Glu Ser Arg Ala Phe
         25                  30                  35

AGC TTC GAT GTA GGA GGG CGT GGA TAT GTC CTG CGG GTA AAT AGC TGC      1577
Ser Phe Asp Val Gly Gly Arg Gly Tyr Val Leu Arg Val Asn Ser Cys
     40                  45                  50

GCC GAT GGT TTC TAC AAA GAT CGT TAT GTT TAT CGG CAC TTT GCA TCG      1625
Ala Asp Gly Phe Tyr Lys Asp Arg Tyr Val Tyr Arg His Phe Ala Ser
 55                  60                  65

GCC GCG CTC CCG ATT CCG GAA GTG CTT GAC ATT GGG GAA TTC AGC GAG      1673
Ala Ala Leu Pro Ile Pro Glu Val Leu Asp Ile Gly Glu Phe Ser Glu
 70              75                  80                  85

AGC CTG ACC TAT TGC ATC TCC CGC CGT GCA CAG GGT GTC ACG TTG CAA      1721
Ser Leu Thr Tyr Cys Ile Ser Arg Arg Ala Gln Gly Val Thr Leu Gln
             90                  95                 100

GAC CTG CCT GAA ACC GAA CTG CCC GCT GTT CTG CAG CCG GTC GCG GAG      1769
Asp Leu Pro Glu Thr Glu Leu Pro Ala Val Leu Gln Pro Val Ala Glu
        105                 110                 115

GCC ATG GAT GCG ATC GCT GCG GCC GAT CTT AGC CAG ACG AGC GGG TTC      1817
Ala Met Asp Ala Ile Ala Ala Ala Asp Leu Ser Gln Thr Ser Gly Phe
        120                 125                 130

GGC CCA TTC GGA CCG CAA GGA ATC GGT CAA TAC ACT ACA TGG CGT GAT      1865
Gly Pro Phe Gly Pro Gln Gly Ile Gly Gln Tyr Thr Thr Trp Arg Asp
    135                 140                 145

TTC ATA TGC GCG ATT GCT GAT CCC CAT GTG TAT CAC TGG CAA ACT GTG      1913
Phe Ile Cys Ala Ile Ala Asp Pro His Val Tyr His Trp Gln Thr Val
150                 155                 160                 165

ATG GAC GAC ACC GTC AGT GCG TCC GTC GCG CAG GCT CTC GAT GAG CTG      1961
Met Asp Asp Thr Val Ser Ala Ser Val Ala Gln Ala Leu Asp Glu Leu
                170                 175                 180

ATG CTT TGG GCC GAG GAC TGC CCC GAA GTC CGG CAC CTC GTG CAC GCG      2009
Met Leu Trp Ala Glu Asp Cys Pro Glu Val Arg His Leu Val His Ala
            185                 190                 195

GAT TTC GGC TCC AAC AAT GTC CTG ACG GAC AAT GGC CGC ATA ACA GCG      2057
Asp Phe Gly Ser Asn Asn Val Leu Thr Asp Asn Gly Arg Ile Thr Ala
        200                 205                 210

GTC ATT GAC TGG AGC GAG GCG ATG TTC GGG GAT TCC CAA TAC GAG GTC      2105
Val Ile Asp Trp Ser Glu Ala Met Phe Gly Asp Ser Gln Tyr Glu Val
        215                 220                 225

GCC AAC ATC TTC TTC TGG AGG CCG TGG TTG GCT TGT ATG GAG CAG CAG      2153
```

```
Ala Asn Ile Phe Phe Trp Arg Pro Trp Leu Ala Cys Met Glu Gln Gln
230                 235                 240                 245

ACG CGC TAC TTC GAG CGG AGG CAT CCG GAG CTT GCA GGA TCG CCG CGG    2201
Thr Arg Tyr Phe Glu Arg Arg His Pro Glu Leu Ala Gly Ser Pro Arg
                250                 255                 260

CTC CGG GCG TAT ATG CTC CGC ATT GGT CTT GAC CAA CTC TAT CAG AGC    2249
Leu Arg Ala Tyr Met Leu Arg Ile Gly Leu Asp Gln Leu Tyr Gln Ser
            265                 270                 275

TTG GTT GAC GGC AAT TTC GAT GAT GCA GCT TGG GCG CAG GGT CGA TGC    2297
Leu Val Asp Gly Asn Phe Asp Asp Ala Ala Trp Ala Gln Gly Arg Cys
            280                 285                 290

GAC GCA ATC GTC CGA TCC GGA GCC GGG ACT GTC GGG CGT ACA CAA ATC    2345
Asp Ala Ile Val Arg Ser Gly Ala Gly Thr Val Gly Arg Thr Gln Ile
            295                 300                 305

GCC CGC AGA AGC GCG GCC GTC TGG ACC GAT GGC TGT GTA GAA GTA CTC    2393
Ala Arg Arg Ser Ala Ala Val Trp Thr Asp Gly Cys Val Glu Val Leu
310                 315                 320                 325

GCC GAT AGT GGA AAC CGA CGC CCC AGC ACT CGT CCG AGG GCA AAG GAA    2441
Ala Asp Ser Gly Asn Arg Arg Pro Ser Thr Arg Pro Arg Ala Lys Glu
                330                 335                 340

TAGTGAGGTA CCTAATAGTG AGATCCAACA CTTACGTTTG CAACGTCCAA GAGCAAATAG    2501

ACCACGACGC CGGAAGGTTG CCGCAGCGTG TGGATTGCGT CTCAATTCTC TCTTGCAGGA    2561

ATGCAATGAT GAATATGATA CTGACTATGA AACTTTGAGG GAATACTGCC TAGCACCGTC    2621

ACCTCATAAC GTGCATCATG CATGCCCTGA CAACATGGAA CATCGCTATT TTTCTGAAGA    2681

ATTATGCTCG TTGGAGGATG TCGCGGCAAT TGCAGCTATT GCCAACATCG AACTACCCCT    2741

CACGCATGCA TTCATCAATA TTATTCATGC GGGGAAAGGC AAGATTAATC CAACTGGCAA    2801

ATCATCCAGC GTGATTGGTA ACTTCAGTTC CAGCGACTTG ATTCGTTTTG GTGCTACCCA    2861

CGTTTTCAAT AAGGACGAGA TGGTGGAGTA AGAAGGAGT GCGTCGAAGC AGATCGTTCA    2921

AACATTTGGC AATAAAGTTT CTTAAGATTG AATCCTGTTG CCGGTCTTGC GATGATTATC    2981

ATATAATTTC TGTTGAATTA CGTTAAGCAT GTAATAATTA ACATGTAATG CATGACGTTA    3041

TTTATGAGAT GGGTTTTTAT GATTAGAGTC CCGCAATTAT ACATTTAATA CGCGATAGAA    3101

AACAAAATAT AGCGCGCAAA CTAGGATAAA TTATCGCGCG CGGTGTCATC TATGTTACTA    3161

GATCGATCAA ACTTCGGTAC TGTGTAATGA CGATGAGCAA TCGAGAGGCT GACTAACAAA    3221

AGGTACATCG GTCGAC                                                    3237
```

(2) INFORMATION FOR SEQ ID NO:27:

(i) SEQUENCE CHARACTERISTICS:
        (A) LENGTH: 4 amino acids (B) TYPE: amino acid (D) TOPOLOGY: linear (ii) MOLECULE TYPE: peptide (xi) SEQUENCE DESCRIPTION: SEQ ID NO:27:

Met Met Met Pro
1

(2) INFORMATION FOR SEQ ID NO:28:

(i) SEQUENCE CHARACTERISTICS:
        (A) LENGTH: 4 amino acids (B) TYPE: amino acid

```
            (D) TOPOLOGY:  linear (ii) MOLECULE TYPE:  peptide (xi) SEQUENCE DESCRIPTION:  SEQ ID NO:28:

Lys Asp Glu Leu
```